United States Patent
Smith et al.

(10) Patent No.: US 12,031,151 B2
(45) Date of Patent: Jul. 9, 2024

(54) METHODS OF IMPROVING PROTEIN TITER IN CELL CULTURE

(71) Applicant: Regeneron Pharmaceuticals, Inc., Tarrytown, NY (US)

(72) Inventors: Reginald Smith, Schenectady, NY (US); Sarah Nicoletti, Yeong-Gu Incheon (KR); Victor Shashilov, Castleton, NY (US); Hongxia Wang, Briarcliff Manor, NY (US); Jikang Wu, Chappaqua, NY (US); Abdelqader Zamamiri, Glenmont, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 162 days.

(21) Appl. No.: 17/578,681

(22) Filed: Jan. 19, 2022

(65) Prior Publication Data
US 2022/0228107 A1 Jul. 21, 2022

Related U.S. Application Data

(60) Provisional application No. 63/139,494, filed on Jan. 20, 2021.

(51) Int. Cl.
*C12N 5/00* (2006.01)
*C12N 5/071* (2010.01)
*C12N 15/79* (2006.01)

(52) U.S. Cl.
CPC ......... *C12N 5/0018* (2013.01); *C12N 5/0682* (2013.01); *C12N 15/79* (2013.01); *C12N 2500/32* (2013.01); *C12N 2500/60* (2013.01)

(58) Field of Classification Search
CPC .... C12N 5/0018; C12N 5/0682; C12N 15/79; C12N 2500/32; C12N 2500/60; C12N 2511/00; C12N 5/0037
See application file for complete search history.

(56) References Cited

U.S. PATENT DOCUMENTS

2014/0234905 A1* 8/2014 Pia ........................ C12N 5/0043
435/405
2014/0273095 A1 9/2014 Oshodi et al.

FOREIGN PATENT DOCUMENTS

| WO | 2007/076032 A2 | 7/2007 |
| WO | 2013/158279 A1 | 10/2013 |
| WO | 2017/024062 A1 | 2/2017 |

OTHER PUBLICATIONS

Xu, X., Gevaert, B., Bracke, N., Yao, H., Wynendaele, E., & De Spiegeleer, B. (2017). Hydrophilic interaction liquid chromatography method development and validation for the assay of HEPES zwitterionic buffer. Journal of pharmaceutical and biomedical analysis, 135, 227-233. (Year: 2017).*

(Continued)

*Primary Examiner* — Paul J Holland
*Assistant Examiner* — Erica Nicole Jones-Foster
(74) *Attorney, Agent, or Firm* — McCarter & English, LLP

(57) ABSTRACT

Methods of improving recombinant protein titer and cell titer in cell culture using cell culture media having reduced impurities are provided, and well as cell culture media having reduced impurities that can used for the production of a recombinant protein and cells with improved titer. The cell culture media having reduced impurities comprises a HEPES buffer, and the reduced impurities are HEPES related impurities. In certain aspects, methods and media improve protein titer, cell growth, and/or viable cell density.

13 Claims, 8 Drawing Sheets

(56) References Cited

OTHER PUBLICATIONS

Derouzai et al., Serum-free large-scale transient transfection of CHO cells. Biotechnol Bioeng. Aug. 20, 2004;87 (4):537-45.
International Search Report and Written Opinion for Application No. PCT/US2022/012883, dated Apr. 13, 2022, 16 pages.

* cited by examiner

METHODS OF IMPROVING PROTEIN TITER IN CELL CULTURE

This application claims priority to U.S. application Ser. No. 63/139,494, filed Jan. 20, 2021, and is incorporated by reference.

FIELD OF THE INVENTIONS

The inventions relate to methods for culturing of cells to improve titer and for the production of recombinant proteins. The inventions specifically relate to methods for culturing cells to improve titer using media having reduced impurities and for the production of protein biopharmaceuticals, as well as cells and cell cultures grown according to the methods and proteins produced by the cells and cell cultures.

BACKGROUND OF THE INVENTIONS

Biological agents, particularly proteins and polypeptides, are often developed as novel biopharmaceutical products. Engineered cells that produce high levels of a particular protein of interest have become critically important for successful commercial production of these biopharmaceutical products. Control and optimization of cell culture conditions varies and has great effect on the level and quality of the therapeutic protein produced in cell culture.

It is customary to manufacture proteins via cell culture in a batch or fed-batch process. Early stages of inoculum growth after vial thaw include culturing cells in a seed culture. Typically, cells are grown at an exponential growth rate, such as in seed train bioreactors, in order to progressively increase size and/or volume of the cell population. After cell mass is scaled up through several bioreactor stages, cells are then transferred to a fed-batch, production bioreactor while the cells are still in exponential growth (log phase) (Gambhir, A. et al., 2003, *J Bioscience Bioeng* 95(4):317-327).

Following transfer to fed-batch culture, cells are cultured for a period of time whereas the composition of the medium is monitored and controlled to allow production of the protein or polypeptide of interest. After a particular yield is reached or cell viability, waste accumulation or nutrient depletion determines that the culture should be terminated, the produced protein or polypeptide is isolated. Many significant advances have been made over the past decade intending to improve recombinant protein yield, which currently reaches titers of multiple grams per liter. Advancements in protein manufacturing processes, as well as in cell line engineering, and cell culture medium and feed development, have contributed to the gain in protein yield. For instance, schemes to optimize cell culture medium and feed include nutrient supplementation and the design of chemically defined, serum-free media to support continuous cell growth and optimum product secretion.

However, there is still a need in the art for medium and methods for culturing cells, wherein the medium allows for healthy and robust cell growth and maintenance, and high-titer production of recombinant proteins.

SUMMARY OF THE INVENTIONS

In an aspect, a method for improving recombinant protein titer in production of a recombinant protein by culturing recombinant eukaryotic cells is provided. In certain embodiments, the method comprises (a) providing a defined cell culture medium having reduced impurities, the defined cell culture medium comprising a 4-hydroxyethyl piperazine ethanesulfonic acid (HEPES) buffer, and having less than about 4000 ppm of a HEPES related impurity having a molecular weight (MW) of 267.07, relative to the total amount of HEPES buffer in the medium (4000 µmol HEPES impurity MW 267.07/mole of total HEPES), and less than about 400 ppm of a HEPES related impurity having a molecular weight (MW) of 221.06, relative to the total amount of HEPES buffer in the medium (400 µmol HEPES impurity MW 221.06/mole of total HEPES); (b) culturing said recombinant eukaryotic cells in said defined cell culture medium having reduced impurities; (c) expressing a recombinant protein of interest from said recombinant eukaryotic cells; and (d) producing a higher titer of the recombinant protein in the defined cell culture medium having reduced impurities relative to the that of similar or identical cells cultured in non-reduced impurity media.

In certain embodiments, the higher titer of the recombinant protein is increased by at least about 5%, as compared to that of similar or identical cells cultured in non-reduced impurity media.

In certain embodiments, the eukaryotic cell may be a mammalian cell, avian cell, insect cell, or yeast cell. In particular embodiments, the eukaryotic cell may be a CHO cell. In other embodiments, the recombinant protein may be selected an Fc-fusion protein, a receptor-Fc-fusion protein, a trap-type protein, such as a trap protein or a mini-trap protein, an antibody, an antibody fragment, or a ScFv-Fc fusion protein, or any other recombinant protein, including those disclosed in the application.

In certain embodiments, the expressing of the recombinant protein of interest may occur during production phase, growth phase, or both. In other embodiments, the culturing of the recombinant eukaryotic cells in the defined cell culture medium having reduced impurities occurs during production phase, growth phase, or both.

In yet other embodiments, the methods improve cell culture performance, including improvement of cell growth, wherein cell growth during the culturing of the recombinant eukaryotic cells is higher than the cell growth of similar or identical recombinant eukaryotic cells in non-impurity reduced media.

In other aspects of the inventions, a defined cell culture medium having reduced impurities is provided. In certain embodiments, the medium comprises a defined cell culture medium having reduced impurities, the defined cell culture medium comprising a 4-hydroxyethyl piperazine ethanesulfonic acid (HEPES) buffer, and having less than about 800 ppm of a HEPES related impurity having a molecular weight (MW) of 267.07, relative to the total amount of HEPES buffer in the medium (800 µmol HEPES impurity MW 267.07/mole of total HEPES), and less than about 80 ppm of a HEPES related impurity having a molecular weight (MW) of 221.06, relative to the total amount of HEPES buffer in the medium (80 µmol HEPES impurity MW 221.06/mole of total HEPES).

In yet other aspects of the inventions, a method for selecting a defined cell culture medium for use in cell culture to improve cell culture performance is provided. In certain embodiments, the method generally comprises: (a) providing a defined cell culture medium comprising a 4-hydroxyethyl piperazine ethanesulfonic acid (HEPES) buffer; (b) analyzing the defined cell culture medium comprising the HEPES buffer to determine the amount of a HEPES related impurity having a molecular weight (MW) of 267.07 and the amount of a HEPES related impurity having a molecular weight (MW) of 221.06 present in the defined cell culture medium; (c) selecting the defined cell culture medium comprising the HEPES buffer for use in cell culture if the defined cell culture medium comprising the HEPES buffer is determined to have less than about 4000 ppm of the HEPES related impurity having a molecular weight (MW) of 267.07, relative to the total amount of HEPES buffer in the medium (4000 μmol HEPES impurity MW 267.07/mole of total HEPES), and less than about 400 ppm of the HEPES related impurity having a molecular weight (MW) of 221.06, relative to the total amount of HEPES buffer in the medium (400 μmol HEPES impurity MW 221.06/mole of total HEPES); wherein the use of the defined cell culture medium comprising the HEPES buffer having less than about 4000 ppm of the HEPES related impurity having a molecular weight (MW) of 267.07, relative to the total amount of HEPES buffer in the medium (4000 μmol HEPES impurity MW 267.07/mole of total HEPES), and less than about 400 ppm of the HEPES related impurity having a molecular weight (MW) of 221.06, relative to the total amount of HEPES buffer in the medium (400 μmol HEPES impurity MW 221.06/mole of total HEPES) improves cell culture performance, as compared to cell culture performance in non-HEPES related impurity reduced media. In certain embodiments, the improved cell culture performance includes improved cell culture titer and/or cell growth.

In yet other aspects of the inventions, a method for selecting a HEPES buffer for use in cell culture to improve cell culture performance is provided. In certain embodiments, the method generally comprises: (a) providing a 4-hydroxyethyl piperazine ethanesulfonic acid (HEPES) buffer; (b) analyzing the HEPES buffer to determine the amount of a HEPES related impurity having a molecular weight (MW) of 267.07 and the amount of a HEPES related impurity having a molecular weight (MW) of 221.06 present in the HEPES buffer; (c) selecting the HEPES buffer for use in cell culture if the HEPES buffer is determined to have less than about 4000 ppm of the HEPES related impurity having a molecular weight (MW) of 267.07, relative to the total amount of HEPES buffer to be used in connection with the cell culture (4000 μmol HEPES impurity MW 267.07/mole of total HEPES), and less than about 400 ppm of the HEPES related impurity having a molecular weight (MW) of 221.06, relative to the total amount of HEPES buffer to be used in connection with the cell culture; wherein the use of the HEPES buffer having less than about 4000 ppm of the HEPES related impurity having a molecular weight (MW) of 267.07, relative to the total amount of HEPES buffer to be used in connection with the cell culture (4000 μmol HEPES impurity MW 267.07/mole of total HEPES), and less than about 400 ppm of the HEPES related impurity having a molecular weight (MW) of 221.06, relative to the total amount of HEPES buffer to be used in connection with the cell culture (400 μmol HEPES impurity MW 221.06/mole of total HEPES) improves cell culture performance, as compared to cell culture performance in the presence of HEPES buffer having higher amounts of said impurities. In certain embodiments, the improved cell culture performance includes improved cell culture titer and/or cell growth.

Other aspects of the inventions provide cell cultures comprising (i) at least one recombinant eukaryotic cell that can express a recombinant protein and (ii) a cell culture medium, wherein the cell culture is produced by a method comprising the steps of: (a) providing a defined cell culture medium having reduced impurities, the defined cell culture medium having less than about 4000 μmol of a HEPES related impurity having a molecular weight of 267.07 per mole of total HEPES, and less than about 400 μmol of a HEPES related impurity having a molecular weight of 221.06 per mole of total HEPES; (b) culturing said recombinant eukaryotic cells in said defined cell culture medium having reduced impurities; (c) expressing a recombinant protein of interest from said recombinant eukaryotic cells; and (d) producing a higher titer of the recombinant protein in the defined cell culture medium having reduced impurities relative to the that of similar or identical cells cultured in non-reduced impurity media.

The eukaryotic cell can be selected from the group consisting of mammalian cell, avian cell, insect cell, and yeast cell, can be selected from the group consisting of CHO, COS, retinal cell, Vero, CV1, kidney, HeLa, HepG2, WI38, MRC 5, Colo25, HB 8065, HL-60, lymphocyte, A431, CV-1, U937, 3T3, L cell, C127 cell, SP2/0, NS-0, MMT cell, stem cell, tumor cell, and a cell line derived from an aforementioned cell. For example, the eukaryotic cell can be a CHO cell.

The expressing of a recombinant protein of interest can occur during production phase, growth phase, or both. The culturing of the recombinant eukaryotic cells in said defined cell culture medium having reduced impurities can occur during production phase, growth phase, or both. The cell growth during said culturing of the recombinant eukaryotic cells can be higher than the cell growth of similar or identical recombinant eukaryotic cells in non-impurity reduced media. The higher titer of the recombinant protein can increased by at least about 5%, as compared to that of similar or identical cells cultured in non-reduced impurity media.

The recombinant protein can comprise an Fc domain. The recombinant protein can be an antibody, a human antibody, a humanized antibody, a chimeric antibody, a monoclonal antibody, a multispecific antibody, a bispecific antibody, an antibody fragment, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody, the recombinant protein is selected from the group consisting of an anti-PD1 antibody, an anti-PDL-1 antibody, an anti-Dll4 antibody, an anti-ANG2 antibody, an anti-AngPtl3 antibody, an anti-PDGFR antibody, an anti-Erb3 antibody, an anti-PRLR antibody, an anti-TNF antibody, an anti-EGFR antibody, an anti-PCSK9 antibody, an anti-GDF8 antibody, an anti-GCGR antibody, an anti-VEGF antibody, an anti-IL1R antibody, an anti-IL4R antibody, an anti-IL6R antibody, an anti-IL1 antibody, an anti-IL2 antibody, an anti-IL3 antibody, an anti-IL4 antibody, an anti-IL5 antibody, an anti-IL6 antibody, an anti-IL7 antibody, an anti-RSV antibody, an anti-NGF antibody, an anti-CD3 antibody, an anti-CD20 antibody, an anti-CD19 antibody, an anti-CD28 antibody, an anti-CD48 antibody, an anti-CD3/anti-CD20 bispecific antibody, an anti-CD3/anti-MUC16 bispecific antibody, and an anti-CD3/anti-PSMA bispecific antibody. For example, the recombinant protein can be selected from the group consisting of alirocumab, atoltivimab, maftivimab, odesivimab, odesivivmab-ebgn, casirivimab, imdevimab, cemiplimab, cemplimab-rwlc, dupilumab, evinacumab, evinacumab-dgnb, fasimumab, nesvacumab, trevogrumab, rinucumab and sarilumab.

The recombinant protein also can be selected from the group consisting of an Fc-fusion protein, a receptor-Fc-fusion protein (TRAP), a mini-trap protein and a ScFv-Fc fusion protein or any other recombinant protein.

Other aspects of the inventions provide recombinant proteins produced in a cell culture comprising (i) at least one recombinant eukaryotic cell that can express said recombinant protein and (ii) a cell culture medium, wherein the recombinant protein is produced by a method comprising the steps of: (a) providing a defined cell culture medium having reduced impurities, the defined cell culture medium having less than about 4000 µmol of a HEPES related impurity having a molecular weight of 267.07 per mole of total HEPES, and less than about 400 µmol of a HEPES related impurity having a molecular weight of 221.06 per mole of total HEPES; (b) culturing said recombinant eukaryotic cells in said defined cell culture medium having reduced impurities; (c) expressing a recombinant protein of interest from said recombinant eukaryotic cells; and (d) producing a higher titer of the recombinant protein in the defined cell culture medium having reduced impurities relative to the that of similar or identical cells cultured in non-reduced impurity media.

The eukaryotic cell can be selected from the group consisting of mammalian cell, avian cell, insect cell, and yeast cell, can be selected from the group consisting of CHO, COS, retinal cell, Vero, CV1, kidney, HeLa, HepG2, WI38, MRC 5, Colo25, HB 8065, HL-60, lymphocyte, A431, CV-1, U937, 3T3, L cell, C127 cell, SP2/0, NS-0, MMT cell, stem cell, tumor cell, and a cell line derived from an aforementioned cell. For example, the eukaryotic cell can be a CHO cell.

The expressing of a recombinant protein of interest can occur during production phase, growth phase, or both. The culturing of the recombinant eukaryotic cells in said defined cell culture medium having reduced impurities can occur during production phase, growth phase, or both. The cell growth during said culturing of the recombinant eukaryotic cells can be higher than the cell growth of similar or identical recombinant eukaryotic cells in non-impurity reduced media. The higher titer of the recombinant protein can increased by at least about 5%, as compared to that of similar or identical cells cultured in non-reduced impurity media.

The recombinant protein can comprise an Fc domain. The recombinant protein can be an antibody, a human antibody, a humanized antibody, a chimeric antibody, a monoclonal antibody, a multispecific antibody, a bispecific antibody, an antibody fragment, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. the recombinant protein is selected from the group consisting of an anti-PD1 antibody, an anti-PDL-1 antibody, an anti-Dll4 antibody, an anti-ANG2 antibody, an anti-AngPtl3 antibody, an anti-PDGFR antibody, an anti-Erb3 antibody, an anti-PRLR antibody, an anti-TNF antibody, an anti-EGFR antibody, an anti-PCSK9 antibody, an anti-GDF8 antibody, an anti-GCGR antibody, an anti-VEGF antibody, an anti-IL1R antibody, an anti-IL4R antibody, an anti-IL6R antibody, an anti-IL1 antibody, an anti-IL2 antibody, an anti-IL3 antibody, an anti-IL4 antibody, an anti-IL5 antibody, an anti-IL6 antibody, an anti-IL7 antibody, an anti-RSV antibody, an anti-NGF antibody, an anti-CD3 antibody, an anti-CD20 antibody, an anti-CD19 antibody, an anti-CD28 antibody, an anti-CD48 antibody, an anti-CD3/anti-CD20 bispecific antibody, an anti-CD3/anti-MUC16 bispecific antibody, and an anti-CD3/anti-PSMA bispecific antibody. For example, the recombinant protein can be selected from the group consisting of alirocumab, atoltivi-mab, maftivimab, odesivimab, odesivivmab-ebgn, casirivimab, imdevimab, cemiplimab, cemplimab-rwlc, dupilumab, evinacumab, evinacumab-dgnb, fasimumab, nesvacumab, trevogrumab, rinucumab and sarilumab.

The recombinant protein also can be selected from the group consisting of an Fc-fusion protein, a receptor-Fc-fusion protein (TRAP), a mini-trap protein and a ScFv-Fc fusion protein, or any other recombinant protein.

Cells, cell cultures, recombinant proteins and methods according to the inventions are provided.

While multiple embodiments are disclosed throughout this application, still other embodiments of the present inventions will become apparent to those skilled in the art from the following detailed description, which shows and describes illustrative embodiments of the inventions. As will be realized, the inventions are capable of modifications in various aspects, all without departing from the spirit and scope of the present inventions. Accordingly, the detailed description are to be regarded as illustrative in nature and not restrictive.

BRIEF DESCRIPTION OF THE DRAWINGS

FIG. 2A is based on data from Site 1. FIG. 2B is based on data from Site 2. FIG. 2A has a data point overlap towards the right side, which also is depicted in FIG. 1 at lot 1117000128 and lot 1117000130.

FIG. 4A is based on data from Site 1. FIG. 4B is based on data from Site 2. FIG. 4A has two data point overlaps. The first overlap is near the middle, which also is depicted in FIG. 3 at lot 1117000129 and lot 1117000138. The second overlap is towards the right side, which also is depicted in FIG. 3 at lot 1117000128 and lot 1117000130.

Figure 1:
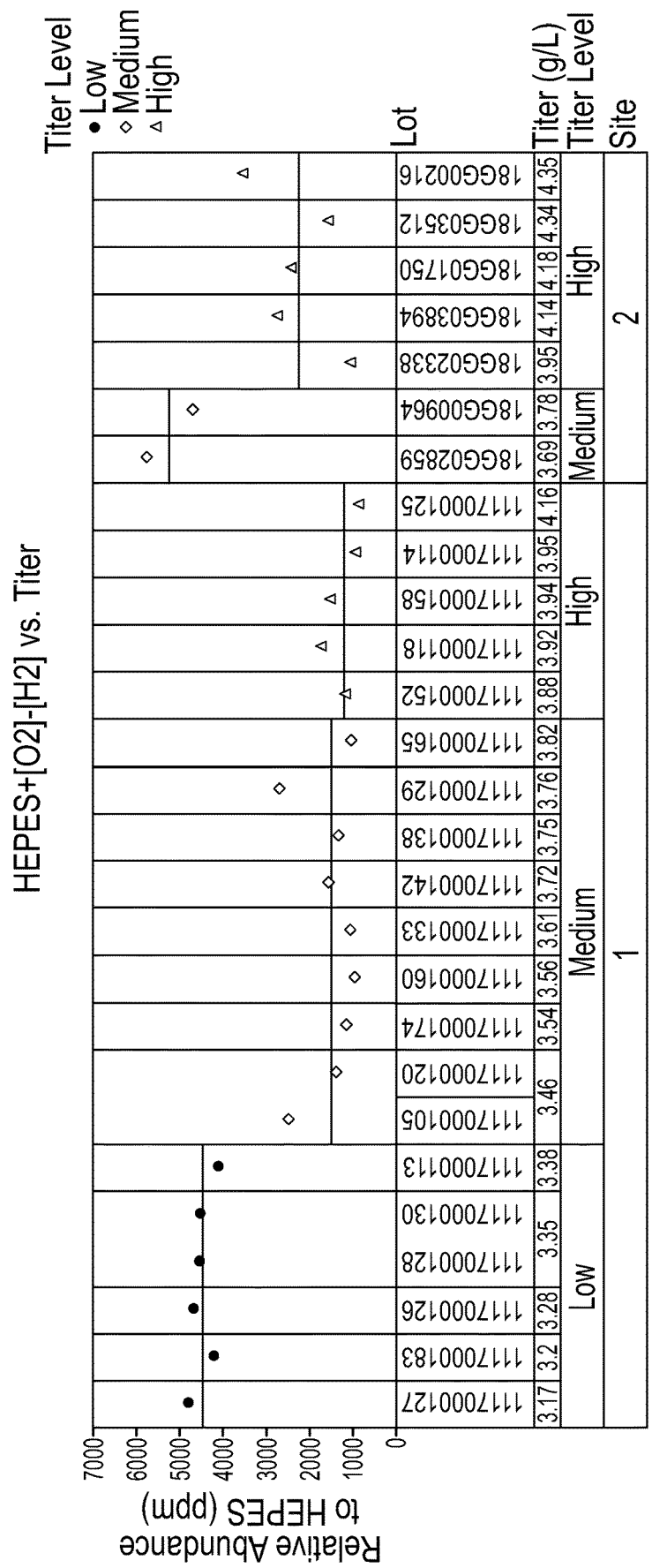
FIG. 1 illustrates the relation between a HEPES related impurity and protein titer, in accordance with one embodiment of the inventions.

The following examples are provided for illustrative purposes only and are not intended to limit the scope of the inventions.

DETAILED DESCRIPTION OF THE INVENTIONS

It accordance with aspects of the inventions, it has been unexpectedly found that use of a cell culture medium with reduced impurities improves cell culture performance, including improvements in cell growth and protein production by a cell in a cell culture, relative to a cell culture medium that does not have such reduced impurities.

More particularly, it has unexpectedly been found that impurities in cell culture medium comprising 4-hydroxyethyl piperazine ethanesulfonic acid (HEPES) buffer impact cell culture performance. In accordance with the inventions, HEPES related impurities have been identified that impact, i.e., exhibit a strong negative correlation to, cell culture performance (e.g., protein titer). In one embodiment, the HEPES related impurities comprise a HEPES related impurity having a molecular weight (MW) of 267.07, a HEPES related impurity having a molecule weight of 221.06, and combinations thereof. In certain embodiments, it was discovered that use of a cell culture medium with reduced amounts of these HEPES related impurities improves cell culture performance, as compared to a cell culture medium that does not have such reduced amounts of HEPES related impurities.

The section headings used herein are for organizational purposes only and are not to be construed as limiting the subject matter described. The methods and techniques described herein are generally performed according to conventional methods known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), Harlow and Lane Antibodies: A Laboratory Manual, Cold Spring Harbor Laboratory Press, Cold Spring Harbor, N.Y. (1990), and Julio E. Celis, Cell Biology: A Laboratory Handbook, 2nd ed., Academic Press, New York, N.Y. (1998), and Dieffenbach and Dveksler, PCR Primer: A Laboratory Manual, Cold Spring Harbor Laboratory Press, Cold Spring Harbor, N.Y. (1995).

Definitions

Unless defined otherwise, all technical and scientific terms used herein have the same meaning as commonly understood by one of ordinary skill in the art to which this inventions belongs. Although any methods and materials similar or equivalent to those described herein can be used in the practice of the present inventions, particular methods and materials are now described.

The term "about" in the context of numerical values and ranges refers to values or ranges that approximate or are close to the recited values or ranges such that the inventions can perform as intended, such as having a desired rate, amount, degree, increase, decrease, or extent of expression, concentration, or time, as is apparent from the teachings contained herein. Thus, this term encompasses values beyond those simply resulting from systematic error.

The terms "peptide," "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs. Peptides, polypeptides, and proteins include, among other things, antibodies and chimeric or fusion proteins. Peptides, polypeptides, and proteins are produced by recombinant animal cell lines using cell culture methods.

The term "heterologous polynucleotide sequence", as used herein refers to nucleic acid polymers encoding proteins of interest, such as chimeric proteins (like trap molecules), antibodies or antibody portions (e.g., VH, VL, CDR3) that are produced as a biopharmaceutical drug substance. The heterologous polynucleotide sequence may be manufactured by genetic engineering techniques (e.g., such as a sequence encoding a chimeric protein, or a codon-optimized sequence, an intronless sequence, et cetera) and introduced into the cell, where it may reside as an episome or be integrated into the genome of the cell. The heterologous polynucleotide sequence may be a naturally occurring sequence that is introduced into an ectopic site within the production cell genome. The heterologous polypeptide sequence may be a naturally occurring sequence from another organism, such as a sequence encoding a human ortholog.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) *PNAS USA* 90:6444-6448; Poljak et al. (1994) *Structure* 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" is intended to include antibodies having variable and constant regions derived from human germline immunoglobulin sequences. The human antibodies of the inventions may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., *Proc. Natl. Acad. ScL USA* 88: 10535, 1991; Byrn et al., *Nature* 344:677, 1990; and Hollenbaugh et al., "Construction of Immunoglobulin Fusion Proteins", in *Current Protocols in Immunology*, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap comprising an Fc, such as for example an IL-1 trap (e.g., rilonacept, which contains the IL-1RAcP ligand binding region fused to the IL-1R1 extracellular region fused to Fc of hIgG1; see U.S. Pat. No. 6,927,044), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

Additionally, mini-traps are included, which are trap proteins that use a multimerizing component (MC) instead of a Fc portion, and are disclosed in U.S. Pat. Nos. 7,279,159 and 7,087,411.

Derivatives, components, domains, chains and fragments of the above also are included.

All numerical limits and ranges set forth herein include all numbers or values thereabout or there between of the numbers of the range or limit. The ranges and limits described herein expressly denominate and set forth all integers, decimals and fractional values defined and encompassed by the range or limit. Thus, a recitation of ranges of values herein are merely intended to serve as a shorthand method of referring individually to each separate value falling within the range, unless otherwise indicated herein, and each separate value is incorporated into the specification as if it were individually recited herein.

Cell Culture Medium

In one aspect, the present inventions provide a cell culture medium with reduced impurities. In certain embodiments, the cell culture medium comprises 4-hydroxyethyl piperazine ethanesulfonic acid (HEPES) buffer, and the reduced impurities are HEPES related impurities. In certain embodiments, the cell culture medium may be a chemically defined cell culture medium, as discussed herein.

More particularly, in accordance with the inventions, the cell culture medium includes less than about 4000 ppm of a HEPES related impurity having a molecular weight (MW) of 267.07, relative to the amount of HEPES buffer present in the cell culture medium (4000 μmol HEPES impurity MW 267.07/mole of total HEPES), and less than 400 ppm of a HEPES related impurity having a molecular weight (MW) of 221.06, relative to the amount of HEPES buffer present in the cell culture medium (400 μmol HEPES impurity MW 221.06/mole of total HEPES).

At most biological pHs, HEPES is a zwitterionic sulfonic acid buffering agent, and is generally effective as a buffer at pH 6.8 to 8.2. HEPES is widely used in cell culture, in part due to its ability to maintain physiological pH despite changes in carbon dioxide concentration when compared to bicarbonate buffers. Buffer strength for cell culture applications is usually in the range of 10 to 25 mM. A buffer solution of HEPES can be prepared by any of several methods. For instance, the HEPES free acid can be added to water, then titrated with approximately one-half mole equivalent of sodium hydroxide or potassium hydroxide to the pH desired, a simple mixing table for preparing 0.05 M HEPES/NaOH has been published. Alternatively, equimolar concentrations of HEPES free acid and of sodium HEPES can be mixed in approximately equal volumes, back-titrating with either solution to the appropriate pH. Other forms of HEPES include potassium HEPES and hemisodium HEPES. Any suitable HEPES buffer may be used in connection with the present inventions, such that the HEPES buffer has the reduced impurities discussed herein.

The terms "cell culture medium" and "culture medium" refer to a nutrient solution used for growing cells, e.g., eukaryotic cells, that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Chemically defined medium is entirely free of animal-derived components, such as serum- or animal-derived peptones. In one embodiment, the medium is a chemically defined medium.

The medium may also contain components that enhance growth and/or survival above the minimal rate, including hormones and growth factors. The medium is preferably formulated to a pH and salt concentration optimal for cell survival and proliferation.

In certain aspects, the cell culture medium may be serum-free. "Serum-free" applies to a cell culture medium that does not contain animal sera, such as fetal bovine serum. The serum-free media may contain≤16 g/L of hydrolysates, such as soy hydrolysate. The present inventions also provide chemically defined media with reduced impurities, which is not only serum-free, but also hydrolysate-free. "Hydrolysate-free" applies to cell culture media that contains no exogenous protein hydrolysates such as animal or plant protein hydrolysates such, for example peptones, tryptones and the like.

"Base medium" is the initial medium (e.g., present in the seed train and/or at day 0 of the cell culture production) in which the cells are propagated and contains all the necessary nutrients, which includes a base mixture of amino acids. Various recipes (i.e. formulations) for base media may be manufactured or purchased in commercially available lots. Likewise "base feed medium" contains mixtures of supplemental nutrients that are commonly consumed during a production culture and are utilized in a feeding strategy (for a so-called "fed-batch" culture). Varieties of base feed media are commercially available. A "feed" includes scheduled additions or additions to media at regular intervals, such as according to a protocol, including a continuous feed culture system, as in a chemostat (see C. Altamirano et al., *Biotechnol Prog.* 2001 November-December; 17(6):1032-41), or according to a fed-batch process (Y. M. Huang et al., *Biotechnol Prog.* 2010 September-October; 26(5): 1400-10). For example, a culture may be fed once per day, every other day, every three days, or may be fed when the concentration of a specific medium component, which is being monitored, falls outside a desired range.

Without intending to be limited, the inventions may be practiced with any one or more of a variety of base media or combinations thereof. Base media are generally known in the art and include inter alia Eagle's MEME (minimal essential media) (Eagle, Science, 1955, 112(3168):501-504), Ham's F12 (Ham, *Proc. Nat'l. Acad. Sci.* USA, 1965, 53:288-293), F-12 K medium, Dulbecco's medium, Dulbecco's Modified Eagle Medium (*Proc. Natl. Acad. Sci. USA.,* 1952 August; 38(8): 747-752), DMEM/Ham's F12 1:1, Trowell' s T8, A2 media (Holmes and Wolf, *Biophys. Biochem. Cytol.,* 1961, 10:389-401), Waymouth media (Davidson and Waymouth, *Biochem. J.,* 1945, 39(2):188-199), Williams E media (William's et al., *Exp. Cell Res.,* 1971, 69:105 et seq.), RPMI 1640 (Moore et al., *J. Amer. Med. Assoc.,* 1967, 199:519-524), MCDB 104/110 media (Bettger et al., *Proc. Nat'l. Acad. Sci. USA,* 1981, 78(9):5588-5592), Ventrex HL-1 media, albumin-globulin media (Orr et al., *Appl. Microbiol.,* 1973, 25(1):49-54), RPMI-1640 Medium, RPMI-1641 Medium, Iscove's Modified Dulbecco's Medium, McCoy's 5 A Medium, Leibovitz's L-15 Medium, and serum-free media such as EX-CELL™ 300 Series (JRH Biosciences, Lenexa, Kans.), protamine-zinc-insulin media (Weiss et al., 1974, U.S. Pat. No. 4,072,565), biotin-folate media (Cartaya, 1978, US Re30,985), Transferrin-fatty acid media (Baker, 1982, U.S. Pat. No. 4,560,655), transferrin-EGF media (Hasegawa, 1982, U.S. Pat. No. 4,615,977; Chessebeuf, 1984, U.S. Pat. No. 4,786,599), and other media permutations (see Inlow, U.S. Pat. No. 6,048,728; Drapeau, U.S. Pat. No. 7,294,484; Mather, U.S. Pat. No. 5,122,469; Furukawa, U.S. Pat. No. 5,976,833; Chen, U.S. Pat. No. 6,180,401; Chen, U.S. Pat. No. 5,856,179; Etcheverry, U.S. Pat. No. 5,705,364; Etcheverry, U.S. Pat. No. 7,666,416; Ryll, U.S. Pat. No. 6,528,286; Singh, U.S. Pat. No. 6,924,124; Luan, U.S. Pat. No. 7,429,491; and the like).

In certain embodiments, the cell culture medium having reduced impurities of the inventions comprise a base medium containing all necessary nutrients for a viable cell culture and HEPES buffer. The HEPES buffer may be a component of the base medium, or it may be added to the cell culture medium. In accordance with aspects of the inventions, the cell culture medium having reduced impurities includes less than about 4000 ppm of a HEPES related impurity having a molecular weight (MW) of 267.07, relative to the amount of a HEPES buffer present in the cell culture medium (4000 µmol HEPES impurity MW 267.07/ mole of total HEPES), and less than 400 ppm of HEPES related impurity having a molecular weight (MW) of 221.06, relative to the amount of HEPES buffer present in the cell culture medium (400 µmol HEPES impurity MW 221.06/ mole of total HEPES).

By way of example, an amount of a HEPES related impurity relative to the amount of HEPES buffer present generally relates to the abundance of the impurity normalized to the HEPES in the medium. For instance, relative amounts may be determined using standard analytical techniques, such as HPLC, LC-MS, etc., wherein relative amount (Impurity, ppm)=Peak area (Impurity)/Peak area (HEPES+HEPES dimer+HEPES adducts)×1,000,000.

In certain embodiments, the medium includes less than about 4000 ppm, less than about 3500 ppm, less than about 3200 ppm, less than about 3000 ppm, less than about 2900 ppm, less than about 2500 ppm, less than about 2200 ppm, less than about 2000 ppm, less than about 1800 ppm, less than about 1500 ppm, less than about 1200 ppm, less than about 1000 ppm, less than about 800 ppm, etc. of a HEPES related impurity having a molecular weight (MW) of 267.07, relative to the amount of HEPES buffer present in the cell culture medium. In other words, less than about 4000 µmol, less than about 3500 µmol, less than about 3200 µmol, less than about 3000 µmol, less than about 2900 µmol, less than about 2500 µmol, less than about 2200 µmol, less than about 2000 µmol, less than about 1800 µmol, less than about 1500 µmol, less than about 1200 µmol, less than about 1000 µmol, less than about 800 µmol, etc. of a HEPES impurity having a MW of 267.07 per mole of total HEPES. In certain embodiments, the medium includes less than about 500 ppm, less than about 450 ppm, less than about 400 ppm, less than about 390 ppm, less than about 370 ppm, less than about 350 ppm, less than about 320 ppm, less than about 300 ppm, less than about 250 ppm, less than about 200 ppm, less than about 150 ppm, less than about 100 ppm, less than about 80 ppm, less than about 75 ppm, less than about 70 ppm, etc. of a HEPES related impurity having a molecular weight (MW) of 221.06, relative to the amount of HEPES buffer present in the cell culture medium. In other words, less than about 500 µmol, less than about 450 µmol, less than about 400 µmol, less than about 390 µmol, less than about 370 µmol, less than about 350 µmol, less than about 320 µmol, less than about 300 µmol, less than about 250 µmol, less than about 200 µmol, less than about 150 µmol, less than about 100 µmol, less than about 80 µmol, less than about 75 µmol, less than about 70 µmol, etc. of a HEPES impurity having a MW of 221.06 per mole of total HEPES.

In certain embodiments, the medium includes less than about 4000 ppm of a HEPES related impurity having a molecular weight (MW) of 267.07, relative to the amount of HEPES buffer present in the cell culture medium (4000 µmol HEPES impurity MW 267.07/mole of total HEPES), and less than 400 ppm of a HEPES related impurity having a molecular weight (MW) of 221.06, relative to the amount of HEPES buffer present in the cell culture medium (400 µmol HEPES impurity MW 221.06/mole of total HEPES). In other embodiments, the medium includes less than about 3900 ppm of a HEPES related impurity having a molecular weight (MW) of 267.07, relative to the amount of HEPES buffer present in the cell culture medium, and less than 390 ppm of a HEPES related impurity having a molecular weight (MW) of 221.06, relative to the amount of HEPES buffer present in the cell culture medium. In yet embodiments, the medium includes less than about 800 ppm of a HEPES related impurity having a molecular weight (MW) of 267.07, relative to the amount of HEPES buffer present in the cell culture medium, and less than 80 ppm of a HEPES related impurity having a molecular weight (MW) of 221.06, relative to the amount of HEPES buffer present in the cell culture medium. As used herein, 1 ppm HEPES impurity=1 µmol HEPES impurity/mole total HEPES.

In other embodiments, the HEPES buffer itself has reduced HEPES related impurities, as described herein. For instance, the HEPES buffer may include less than about 4000 ppm, less than about 3500 ppm, less than about 3200 ppm, less than about 3000 ppm, less than about 2900 ppm, less than about 2500 ppm, less than about 2200 ppm, less than about 2000 ppm, less than about 1800 ppm, less than about 1500 ppm, less than about 1200 ppm, less than about 1000 ppm, less than about 800 ppm, etc. of a HEPES related impurity having a molecular weight (MW) of 267.07, relative to the total amount of HEPES buffer to be used in connection with the cell culture (e.g., in the media). In other words, less than about 4000 µmol, less than about 3500 µmol, less than about 3200 µmol, less than about 3000 µmol, less than about 2900 µmol, less than about 2500 µmol, less than about 2200 µmol, less than about 2000 µmol, less than about 1800 µmol, less than about 1500 µmol, less than about 1200 µmol, less than about 1000 µmol, less than about 800 µmol, etc. of a HEPES impurity having a MW of 267.07 per mole of total HEPES. In certain embodiments, the medium includes less than about 500 ppm, less than about 450 ppm, less than about 400 ppm, less than about 390 ppm, less than about 370 ppm, less than about 350 ppm, less than about 320 ppm, less than about 300 ppm, less than about 250 ppm, less than about 200 ppm, less than about 150 ppm, less than about 100 ppm, less than about 80 ppm, less than about 75 ppm, less than about 70 ppm, etc. of a HEPES related impurity having a molecular weight (MW) of 221.06 relative to the total amount of HEPES buffer to be used in connection with the cell culture (e.g., in the media). In other words, less than about 500 µmol, less than about 450 µmol, less than about 400 µmol, less than about 390 µmol, less than about 370 µmol, less than about 350 µmol, less than about 320 µmol, less than about 300 µmol, less than about 250 µmol, less than about 200 µmol, less than about 150 µmol, less than about 100 µmol, less than about 80 µmol, less than about 75 µmol, less than about 70 µmol, etc. of a HEPES impurity having a MW of 221.06 per mole of total HEPES.

More specifically, in accordance with aspects of the inventions, the HEPES related impurities have the chemical formula and molecular weight (MW) presented in Table 1.

TABLE 1

| Putative ID | Formula | m/z (Negative) |
|---|---|---|
| HEPES+[O2]−[H2] | C8 H16 N2 O6 S | 267.07 |
| HEPES−[CH4] | C7 H14 N2 O4 S | 221.06 |

While not intending to be limited by theory, based on the chemical formula and molecular weight (MW), the following chemical structures are proposed for the HEPES related impurities. However, the inventions are not limited to the presentation of these proposed chemical structures, and other chemical structures corresponding to the chemical formulas and molecular weight (MW) of the HEPES related impurities are envisioned as within the scope of the inventions.

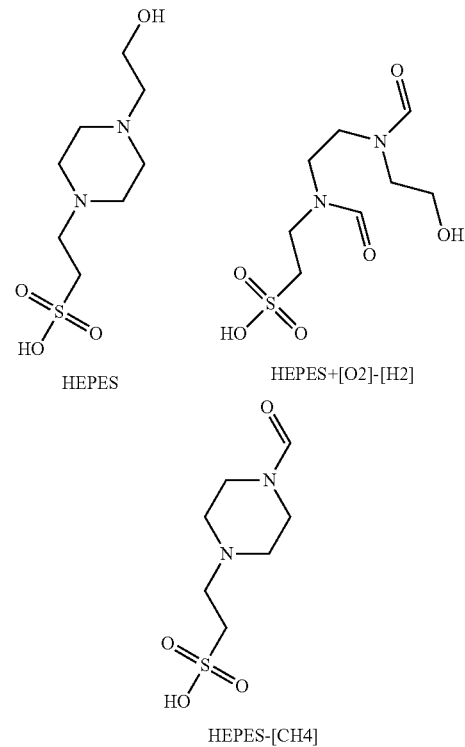

The cell culture medium may also be fed periodically (as in so-called "fed-batch" cultures), with or without additional ingredients such as polyamines or increased concentrations of components like amino acids, salts, sugars, vitamins, hormones, growth factors, buffers, antibiotics, lipids, trace elements and the like, depending on the requirements of the cells to be cultured or the desired cell culture parameters.

In certain aspects, the cell culture medium may be depleted of amino acids over the course of the recombinant protein production, where no additional amino acid supplementation is provided, or the cell culture medium may be "non-depleted", where amino acid supplementation is provided for the depleted amino acids (as described below).

In one embodiment, the medium additionally contains 100 μM±15 μM ornithine, or 300 μM±45 μM ornithine, or 600 μM±90 μM ornithine, or even 900 μM±135 μM ornithine. In another embodiment, the medium contains at least about 5 mg/L±1 mg/L ornithine.HCl, or at least about, 10 mg/L±2 mg/L ornithine.HCl, 15 mg/L±2.25 mg/L ornithine.HCl, or at least about 50 mg/L±7.5 mg/L ornithine.HCl, or at least about 100 mg/L±15 mg/L ornithine.HCl, or at least about 150 mg/L±22.5 mg/L ornithine.HCl.

Putrescine may optionally be added to the supplemented media. Putrescine has been included, at very low concentrations, as a component in some cell culture media formulations; see for example WO 2005/028626, which describes 0.02-0.08 mg/L putrescine; U.S. Pat. No. 5,426,699 (0.08 mg/L); U.S. Pat. No. RE30,985 (0.16 mg/L); U.S. Pat. No. 5,811,299 (0.27 mg/L); U.S. Pat. No. 5,122,469 (0.5635 mg/L); U.S. Pat. No. 5,063,157 (1 mg/L); WO 2008/154014 (~100 82 M-~1000 μM); US Pat. App. No. 2007/0212770 (0.5-30 mg/L polyamine; 2 mg/L putrescine; 2 mg/L putrescine+2 mg/L ornithine; 2 mg/L putrescine+10 mg/L ornithine).

In some embodiments, the cell culture medium is further supplemented with a combination of ornithine and putrescine, wherein the putrescine can be at a concentration of at least about 150 to 720 μM. In some embodiments, the media is further supplemented with putrescine at a concentration of about 170 to 230 μM. In one embodiment, the medium contains 200 μM±30 μM putrescine in addition to ≥90 μM±15 μM ornithine. In one embodiment, the medium contains≤30 mg/L±4.5 mg/L putrescine.2HCl in addition to ≤15 mg/L±2.25 mg/L ornithine. In another embodiment, the medium contains≥30 mg/L±4.5 mg/L putrescine.2HCl in addition to ≥15 mg/L±2.25 mg/L ornithine.HCl. (See International Publication No. WO2014/144198A1, published on Sep. 18, 2014)

In still other embodiments, ornithine is present in the medium at a concentration ranging from 0.09±0.014 mM to 0.9±0.14 mM, such as 0.09±0.014 mM, 0.3±0.05 mM, 0.6±0.09 mM, or 0.9±0.14 mM ornithine. In some embodiments, the medium also contains at least 0.20±0.03 mM putrescine. In some embodiments, the additional putrescine is at a concentration ranging from 0.20±0.03 mM to 0.714±0.11 mM, such as 0.20±0.03 mM, 0.35±0.06, or 0.714±0.11 mM putrescine.

The still other embodiments, the medium may be supplemented with taurine at a concentration (expressed in millimoles per liter) of at least about 0.1, 0.2, 0.3, 0.4, 0.5, 0.6, 0.7, 0.8, 0.9, 1, 2, 3, 4, 5, 6, 7, 8, 9 or 10 mM.

Various other supplements may be added to the culture medium, and are within the skill of the person in the art to determine additionally appropriate conditions. In some embodiments, the medium is supplemented with a mixture of amino acids selected from the group consisting of aspartic acid, cysteine, glutamic acid, glycine, lysine, phenylalanine, proline, serine, threonine, valine, arginine, histidine, asparagine, glutamine, alanine, isoleucine, leucine, methionine, tyrosine, and tryptophan, in order to be non-depleted or as supplemental nutrients are needed.

In one embodiment, the media is further supplemented with about 170 μM to 175 μM nucleosides. In one embodiment, the media contains purine derivatives in a cumulative concentration of at least 40 μM, at least 45 μM, at least 50 μM, at least 55 μM, at least 60 μM, at least 65 μM, at least 70 μM, at least 75 μM, at least 80 μM, at least 85 μM, at least 90 μM, at least 95 μM, at least 100 μM, or at least 105 μM. In one embodiment, the media contains about 100 μM to 110 μM of purine derivatives. Purine derivatives include hypoxanthine and the nucleosides adenosine and guanosine. In one embodiment, the media contains pyrimidine derivatives in a cumulative concentration of at least 30 μM, at least 35 μM, at least 40 μM, at least 45 μM, at least 50 μM, at least 55 μM, at least 60 μM, or at least 65 μM. In one embodiment, the media contains about 65 μM to 75 μM of pyrimidine derivatives. Pyrimidine derivatives include the nucleosides thymidine, uridine, and cytidine. In one particular embodiment, the media contains adenosine, guanosine, cytidine, uridine, thymidine and hypoxanthine.

In addition to the inclusion of any of the above additives, in one embodiment, the media is further supplemented with micromolar amounts of fatty acids (or fatty acid derivatives) and tocopherol. In one embodiment, the fatty acids include any one or more of linoleic acid, linolenic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid, and octanoic acid. In one embodiment, the media contains tocopherol, linoleic acid, and thioctic acid.

In one embodiment, the media also may be further supplemented with a mixture of vitamins, which includes other nutrients and essential nutrients, at a cumulative concentration of at least about 700 μM or at least about 2 mM. In one embodiment, the mixture of vitamins contains one or more of D-biotin, choline chloride, folic acid, myo-inositol, niacinamide, pyridoxine HCl, D-pantothenic acid (hemiCa), riboflavin, thiamine HCl, vitamin B12, and the like. In one embodiment, the mixture of vitamins includes all of D-biotin, choline chloride, folic acid, myo-inositol, niacinamide, pyridoxine HCl, D-pantothenic acid (hemiCa), riboflavin, thiamine HCl, and vitamin B12.

Various embodiments of the media of the inventions having reduced impurities include any of the combinations of the above described embodiments, including chemically defined media, HEPES buffer, plus inter alia (a) amino acids; (b) optionally nucleosides; (c) salts of divalent cations; (d) fatty acids and tocopherol; and (e) vitamins.

In a particular embodiment, the cell culture media with reduced impurities may be chemically defined, and may comprise: HEPES buffer, amino acid mixtures as discussed herein, $CaCl_2$ $2H_2O$; KCl; $MgSO_4$; NaCl; $Na_2HPO_4$ or other phosphate salts; pyruvate; D-biotin; choline chloride; folic acid; myo-inositol; niacinamide; pyridoxine HCl; D-pantothenic acid; riboflavin; thiamine HCl; vitamin B12; p-aminobenzoic acid; ethanolamine HCl; poloxamer 188; DL-a-tocopherol phosphate; linoleic acid; $Na_2SeO_3$; thioctic acid; and glucose; and optionally adenosine; guanosine; cytidine; uridine; thymidine; and hypoxanthine 2Na.

In one embodiment, the starting osmolarity of the media of the inventions is 200-500, 250-400, 275-350, or about 300 mOsm. During growth of the cells in the media of the inventions, and in particular following any feedings according to a fed batch protocol, the osmolarity of the culture may increase up to about 350, 400, 450, 500 or up to about 550 mOsm.

In some embodiments wherein the osmolarity of the medium is less than about 300, the osmolarity may be adjusted to about 300 with the addition of one or more salts in excess of the amount specified. In one embodiment, osmolarity is increased to a desired level by adding one or more of an osmolyte selected from sodium chloride, potassium chloride, a magnesium salt, a calcium salt, an amino acid salt, a salt of a fatty acid, sodium bicarbonate, sodium carbonate, potassium carbonate, a chelator that is a salt, a sugar (e.g., galactose, glucose, sucrose, fructose, fucose, etc.), and a combination thereof. In one embodiment, the osmolyte is added over and above its concentration in a component already present in the defined medium (e.g., a sugar is added over and above the concentration specified for a sugar component).

Each and every embodiment of the media described above, as well as any other media including reduced amounts of the HEPES related impurities as described herein, is referred to as media with reduced impurities or media with reduced HEPES related impurities. Conversely, media including amount of the HEPES related impurities above those levels discussed herein, are hereinafter referred to as non-impurity reduced media or non-HEPES related impurity reduced media. In some embodiments, the non-impurity reduced media comprises the same base media and supplements as the media with reduced impurities, other than the presence of the impurities discussed herein.

Cell Culture

One aspect of the inventions provide a cell culture comprising a cell line expressing a recombinant protein of interest in a medium having reduced impurities, as described herein. Examples of cell lines that are routinely used to produce recombinant proteins include, inter alia, primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, 3T3 cells, 293 cells, Per.C6 cells and chicken embryo cells. In one embodiment, the cell line is a CHO cell line or one or more of several specific CHO cell variants optimized for large-scale protein production, e.g., CHO-K1.

Another aspect of the inventions relate to a methods of culturing cells using the media with reduced impurities as described herein, wherein the use of such media enhances the growth of recombinant eukaryotic cells while improving the titer of one or more recombinant proteins of interest by such cells and maintaining cell viability, in particular by use in the production culture and/or the seed train culture, as compared to culturing of such cells in a non-impurity reduced media.

In some aspects, recombinant protein titer is improved relative to cells grown in non-impurity reduced media. In some embodiments, the protein titer yielded from cell culture in a media having reduced impurities of the inventions is at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22% greater, at least about 23% greater, at least about 24% greater, at least about 25% greater, at least about 26% greater, at least about 27% greater, at least about 28% greater, at least about 29% greater, at least about 30%, at least about 35% greater, at least about 40% greater, or at least about 50% greater than the protein titer (yield) from cells cultured in non-impurity reduced media. In some embodiments, the protein titer yielded form the cell culture in a media having reduced impurities of the inventions are greater than that similar or identical cells cultured in non-impurity reduced media.

In some aspects, cell growth (e.g., doubling rate), viable cell density, cell viability, and combinations thereof, are improved relative to cells grown in non-impurity reduced media.

In some embodiments, the doubling rate of viable cells in media having reduced impurities of the inventions are at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 70%, at least 80%, at least 90%, at least 100%, or at least 3-fold greater than the doubling rate of cells cultured in non-impurity reduced media. In some embodiments, the doubling rate of viable cells in media having reduced impurities of the inventions are about 10%, 11%, 12%, 13%, 14%, 15%, 16%, 17%, 18%, 19%, 20%, 21%, 22%, 23%, 24%, 25%, 26%, 27%, 28%, 29%, or 30% greater than the doubling rate of viable cells in non-impurity reduced media.

In some embodiments, the doubling time of actively cycling mammalian cells is less than 30 hours, less than 29 hours, less than 28 hours, less than 27 hours, less than 26 hours, less than 25 hours, less than 24 hours, less than 23 hours, less than 22 hours, less than 21 hours, less than 20 hours, less than 19 hours, or less than 18 hours in media having reduced impurities. In some embodiments, the doubling time of actively growing mammalian cells is less than 28 hours in media having reduced impurities. In some embodiments, the doubling time of mammalian cells is about 27±1 hours, about 26±1 hours, about 25±1 hours, about 24±1 hours, about 23±1 hours, about 22±1 hours, or about 21±1 hours in media having reduced impurities. In some embodiments, the doubling time of actively cycling mammalian cells is about 24±1 hours in media having reduced impurities. In some embodiments, the doubling time of actively dividing cells cultured in media having reduced impurities is at least 15%, at least 16%, at least 17%, at least 18%, at least 19%, at least 20%, or at least 25% shorter than the doubling time of actively cycling cells cultured in a non-reduced impurity media.

Regarding cell viability, cells grown in media having reduced impurities show a viability that is at least 10%, at least 15%, at least 20%, at least 25%, at least 30%, at least 35%, at least 40%, at least 45%, at least 50%, at least, 55%, at least 60%, at least 65%, at least 70%, at least 75%, at least 80%, at least 85%, at least 90%, at least 95%, at least 99%, at least 100%, or at least 3-fold greater than the viability of cells grown in non-impurity reduced media.

In the production culturing vessel or bioreactor, a basal culture medium and cells are supplied to a culturing vessel following a seed culture or growth phase. In certain embodiments, the cell supernatant or cell lysate is harvested following the production culture. In other embodiments, the polypeptide or protein of interest is recovered from the culture medium or cell lysate, or whatever the case may be depending on the location of the protein of interest, using techniques well known in the art A "cell line" refers to a cell or cells that are derived from a particular lineage through serial passaging or subculturing of cells. The term "cells" is used interchangeably with "cell population".

The term "cell" includes any cell that is suitable for expressing a recombinant nucleic acid sequence. Cells include those of eukaryotes, such as non-human animal cells, mammalian cells, human cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: CHO (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, WI38, MRC 5, Colo25, HB 8065, HL-60, lymphocyte, e.g. Jurkat (T lymphocyte) or Daudi (B lymphocyte), A431 (epidermal), CV-1, U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

In the recombinant protein production phase, a "fed-batch cell culture" or "fed-batch culture" refers to a batch culture wherein the animal cells and culture medium are supplied to the culturing vessel initially and additional culture nutrients are slowly fed, continuously or in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture can be further distinguished from perfusion culturing insofar as the supernatant is not removed from the culturing vessel during the process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached.

The phrase "continuous cell culture" when used herein relates to a technique used to grow cells continually, usually in a particular growth phase. For example, if a constant supply of cells is required, or the production of a particular polypeptide or protein of interest is required, the cell culture may require maintenance in a particular phase of growth. Thus, the conditions must be continually monitored and adjusted accordingly in order to maintain the cells in that particular phase.

One aspect of the inventions relate to a seed culture in which a cell population is expanded prior to protein production and harvest in the production culture. In certain embodiments, the cell culture medium having reduced impurities may be used with a seed cell cultures, as further described herein.

Another aspect of the inventions relate to a production culture in which protein is produced and harvested. Prior to production phase, there is typically a growth phase (also known as a seed train or seed culture) wherein all components for cell culturing are supplied to the culturing vessel at the start of the culturing process then cell population is expanded until ready for production scale. As such, the culturing vessel is inoculated with cells at a suitable seeding density for the initial cell growth phase depending on the starting cell line. In some aspects, the cell culture medium having reduced impurities may be used with a seed cell culture to further improve or enhance the productivity of the cells in the subsequent production phase. In other embodiments, the cell culture medium having reduced impurities may be used with a production cell culture, as further described herein.

Culturing vessels include, but are not limited to well plates, T-flasks, shake flasks, stirred vessels, spinner flasks, hollow fiber, air lift bioreactors, and the like. A suitable cell culturing vessel is a bioreactor. A bioreactor refers to any culturing vessel that is manufactured or engineered to manipulate or control environmental conditions. Such culturing vessels are well known in the art.

Bioreactor processes and systems have been developed to optimize gas exchange, to supply sufficient oxygen to sustain cell growth and productivity, and to remove $CO_2$. Maintaining the efficiency of gas exchange is an important criterion for ensuring successful scale up of cell culture and protein production. Such systems are well-known to the person having skill in the art.

In one embodiment, the media is supplemented at intervals during cell culture according to a fed-batch process. Fed-batch culturing is generally known in the art and employed to optimize protein production (see Y. M. Huang et al., *Biotechnol Prog*. 2010 September-October; 26(5): 1400-10). Fed-batch processes are typically used during the production phase.

Supplemental feed may be performed to include additional nutrients, such as vitamins, amino acids and other nutrients as described hereinabove, at intervals at a frequency of every day, or every 2-3 days, for the duration of the production culture. Supplemented feed may be performed (supplemented media containing nutrients are added) at least 2 times, or at least 8 times, throughout the duration of the production culture for a 2 week or more culture. In another embodiment, the supplemental feed could be performed on each day for the duration of the culture. Alternative culture feeding schedules are also envisioned.

Additional amino acid supplementation may also be performed to provide a non-depleted medium, wherein depleted amino acids are determined according to methods known in the art and described herein. When this regime is employed, additional amino acids are supplemented or added at intervals, preferably at a frequency of every day, or every 2-3 days, for the duration of the production culture, depending on the determination of amino acid depletion. In one embodiment, the mixture of additional amino acids to maintain a non-depleted cell culture medium is added to the culture on or about day 1, on or about day 2, on or about day 3, on or about day 4, on or about day 5, on or about day 6, on or about day 7, on or about day 8, on or about day 9, on or about day 10, on or about day 11, on or about day 12, on or about day 13, and on or about day 14, for a 2 week or more culture. Alternative culture feeding schedules are also envisioned.

Eukaryotic cells, such as CHO cells, may be cultured in small scale cultures, such as in 125 ml containers having about 25 mL of media, 250 mL containers having about 50 to 100 mL of media, 500 mL containers having about 100 to 200 mL of media. Alternatively, the cultures can be large scale such as for example 1000 mL containers having about 300 to 1000 mL of media, 3000 mL containers having about 500 mL to 3000 mL of media, 8000 mL containers having about 2000 mL to 8000 mL of media, and 15000 mL containers having about 4000 mL to 15000 mL of media. Cultures for manufacturing can contain 10,000 L of media or more. Large scale cell cultures, such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture. Concentrated feed medium may be based on any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal useful amount. Concentrated feed media are often used in fed batch culture processes.

In some embodiments, the cell culture may be further supplemented with "point-of-use additions", also known as additions, point-of-use ingredients, or point-of-use chemicals, during the course of cell growth or protein production. Point-of-use additions include any one or more of a growth factor or other proteins, a buffer, an energy source, a salt, an amino acid, a metal, and a chelator. Other proteins include transferrin and albumin. Growth factors, which include cytokines and chemokines, are generally known in the art and are known to stimulate cell growth, or in some cases, cellular differentiation. A growth factor is usually a protein (e.g., insulin), a small peptide, or a steroid hormone, such as estrogen, DHEA, testosterone, and the like. In some cases, a growth factor may be a non-natural chemical that promotes cell proliferation or protein production, such as e.g., tetrahydrofolate (THF), methotrexate, and the like. Non-limiting examples of protein and peptide growth factors include angiopoietins, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin, insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), tumor necrosis factor-alpha (TNF-α), vascular endothelial growth factor (VEGF), wnt signaling pathway agonists, placental growth factor (PlGF), fetal Bovine somatotrophin (FBS), interleukin-1 (IL-1), IL-2, IL-3, IL-4, IL-5, IL-6, IL-7, and the like. In one embodiment, the cell culture media is supplemented with the point-of-use addition growth factor insulin. In one embodiment, the concentration of insulin in the media, i.e., the amount of insulin in the cell culture media after addition, is from about 0.1 µM to 10 µM.

Buffers are generally known in the art. The inventions are not restricted to any particular buffer or buffers, and any one of ordinary skill in the art can select an appropriate buffer or buffer system for use with a particular cell line producing a particular protein. In one embodiment, a point-of-use addition buffer is NaHCO$_3$. In another embodiment, the buffer is HEPES. In other embodiments, the point-of-use addition buffer comprises both NaHCO$_3$ and HEPES. In embodiments wherein the buffer comprises HEPES, the HEPES buffer comprises reduced amounts of the HEPES related impurities, as described herein.

Energy sources for use as a point-of-use addition in cell culture are also well known in the art. Without limitation, in one embodiment, the point-of-use addition energy source is glucose. Given the particular and specific requirements of a particular cell line and the protein to be produced, in one embodiment the glucose can be added to a concentration of about 1 to 20 mM in the media. In some cases, glucose can be added at high levels of 20 g/L or higher.

Chelators are likewise well known in the art of cell culture and protein production. Tetrasodium EDTA dehydrate and citrate are two common chelators used in the art, although other chelators may be employed in the practice of this inventions. In one embodiment, a point-of-use addition chelator is tetrasodium EDTA dihydrate. In one embodiment, a point-of-use addition chelator is citrate, such as Na$_3$C$_6$H$_5$O$_7$.

In one embodiment, the cell culture medium may additionally be supplemented with one or more point-of-use addition amino acids as an energy source, such as e.g., glutamine. In one embodiment, the cell culture media is supplemented with the point-of-use addition glutamine at a final concentration of about 1 mM to 13 mM.

Other point-of-use additions include one or more of various metal salts, such as salts of iron, nickel, zinc and copper. In one embodiment, the cell culture media is supplemented with any one or more of copper sulfate, zinc sulfate, ferric chloride, and nickel sulfate.

Protein Production

In addition to media having reduced impurities and methods of culturing cells in such media, the present inventions provide methods for improving cell culture performance, including improving recombinant protein titer in production of a recombinant protein by culturing recombinant eukaryotic cells. In some embodiments, the recombinant eukaryotic cells comprise a stably integrated nucleic acid encoding the recombinant protein. In other embodiments, the methods of the inventions provide for improved cell growth (e.g., doubling rate), viable cell density, cell viability, and combinations thereof, In some embodiments, the methods of the inventions include providing a cell culture medium having reduced impurities of the inventions, culturing recombinant eukaryotic cells in the medium; expressing a recombinant protein of interest from the recombinant eukaryotic cells, and producing a higher titer of the recombinant protein from the recombinant eukaryotic cells cultured in the medium having reduced impurities relative to similar or identical recombinant eukaryotic cells cultured in non-impurity reduced media.

In some embodiments, the protein production yield or titer, which can be expressed in grams of protein product per liter of culture medium, from cells cultured in medium having reduced impurities is at least 100 mg/L, at least 1 g/L, at least 1.2 g/L, at least 1.4 g/L, at least 1.6 g/L, at least 1.8 g/L, at least 2 g/L, at least 2.5 g/L, at least 3 g/L, at least, 3.5 g/L, at least 4 g/L, at least 4.5 g/L, at least 5 g/L, at least 5.5 g/L, at least 6 g/L, at least 6.5 g/L, at least 7 g/L, at least 7.5 g/L, at least 8 g/L, at least 8.5 g/L, at least 9 g/L, at least 9.5 g/L, at least 10 g/L, at least 15 g/L, or at least 20 g/L.

In some embodiments, the protein titer yielded from cells cultured in medium having reduced impurities is at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23% greater, at least about 24% greater, at least about 25% greater, at least about 26% greater, at least about 27% greater, at least about 28% greater or at least about 29% greater than the protein titer (yield) from similar or identical cells cultured in non-impurity reduced media.

In some embodiments, the titer (yield) of protein by mammalian cells cultured in medium having reduced impurities, described herein, is at least 100 mg/L, at least 0.5 g/L, at least 1 g/L, at least 1.2 g/L, at least 1.4 g/L, at least 1.6 g/L, at least 1.8 g/L, at least 2 g/L, at least 2.5 g/L greater than the titer of protein by a similar or identical cell cultured in non-impurity reduced media.

The methods of the inventions are useful for improving protein production via cell culture processes. The cell lines used in the inventions can be genetically engineered to express a recombinant protein of commercial or scientific interest. Genetically engineering the cell line involves transfecting, transforming or transducing the cells with a recombinant polynucleotide molecule, or otherwise altering (e.g., by homologous recombination and gene activation or fusion of a recombinant cell with a non-recombinant cell) so as to cause the host cell to express a desired recombinant polypeptide. Methods and vectors for genetically engineering cells or cell lines to express a polypeptide of interest are well known to those of skill in the art; for example, various techniques are illustrated in Current Protocols in Molecular Biology. Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69. A wide variety of cell lines suitable for growth in culture are available from the American Type Culture Collection (Manassas, Va.) and commercial vendors.

In some embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. App. Pub. No. US2015/0203579A1), an anti-Programmed Cell Death Ligand-1 (e.g. an anti-PD-L1 antibody as described in in U.S. Pat. App. Pub. No. US2015/0203580A1), an anti-Dll4 antibody, an anti-Angiopoetin-2 antibody (e.g. an anti-ANG2 antibody as described in U.S. Pat. No. 9,402,898), an anti- Angiopoetin-Like 3 antibody (e.g. an anti-AngPtl3 antibody as described in U.S. Pat. No. 9,018,356), an anti-platelet derived growth factor receptor antibody (e.g. an anti-PDGFR antibody as described in U.S. Pat. No. 9,265,827), an anti-Erb3 antibody, an anti-Prolactin Receptor antibody (e.g. anti-PRLR antibody as described in U.S. Pat. No. 9,302,015), an anti-Complement 5 antibody (e.g. an anti-C5 antibody as described in U.S. Pat. App. Pub. No US2015/0313194A1), an anti-TNF antibody, an anti-epidermal growth factor receptor antibody (e.g. an anti-EGFR antibody as described in U.S. Pat. No. 9,132,192 or an anti-EGFRvIII antibody as described in U.S. Pat. App. Pub. No. US2015/0259423A 1), an anti-Proprotein Convertase Subtilisin Kexin-9 antibody (e.g. an anti-PCSK9 antibody as described in U.S. Pat. No. 8,062,640 or U.S. Pat. App. Pub. No. US2014/0044730A1), an anti-Growth And Differentiation Factor-8 antibody (e.g. an anti-GDF8 antibody, also known as anti-myostatin antibody, as described in U.S. Pat. No. 8,871,209 or U.S. Pat. No. 9,260,515), an anti-Glucagon Receptor (e.g. anti-GCGR antibody as described in U.S. Pat. App. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. App. Pub. No. US2014/0271681A1 or U.S. Pat. Nos. 8,735,095 or U.S. Pat. No. 8,945,559), an anti-interleukin 6 receptor antibody (e.g. an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g. anti-IL33 antibody as described in U.S. Pat. App. Pub. Nos. US2014/0271658A1 or US2014/0271642A1), an anti-Respiratory syncytial virus antibody (e.g. anti-RSV antibody as described in U.S. Pat. App. Pub. No. US2014/0271653A1), an anti-Cluster of differentiation 3 (e.g. an anti-CD3 antibody, as described in U.S. Pat. App. Pub. Nos. US2014/0088295A1 and US20150266966A1, and in U.S. application Ser. No. 62/222,605), an anti-Cluster of differentiation 20 (e.g. an anti-CD20 antibody as described in U.S. Pat. App. Pub. Nos. US2014/0088295A1 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. App. Pub. No. US2015/0337029A1), an anti-Ebola virus antibody (e.g. as described in U.S. Pat. App. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. App. Pub. No. US2016/0017029 and U.S. Pat. Nos. 8,309,088 and 9,353,176) and an anti-Activin A antibody. In some embodiments, the bispecific antibody is selected from the group consisting of an anti-CD3×anti-CD20 bispecific antibody (as described in U.S. Pat. App. Pub. Nos. US2014/0088295A1 and US20150266966A1), an anti-CD3×anti-Mucin 16 bispecific antibody (e.g., an anti-CD3×anti-Muc 16 bispecific antibody), and an anti-CD3×anti-Prostate-specific membrane antigen bispecific antibody (e.g., an anti-CD3×anti-PSMA bispecific antibody).

In some embodiments, the protein of interest is selected from the group consisting of alirocumab, atoltivimab, maftivimab, odesivimab, odesivivmab-ebgn, casirivimab, imdevimab, cemiplimab, cemplimab-rwlc, dupilumab, evinacumab, evinacumab-dgnb, fasimumab, nesvacumab, trevogrumab, rinucumab and sarilumab.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,044), or a VEGF trap (e.g., aflibercept or ziv-aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

Additionally, mini-traps are included, which are trap proteins that use a multimerizing component (MC) instead of a Fc portion, and are disclosed in U.S. Pat. Nos. 7,279,159 and 7,087,411.

Derivatives, components, domains, chains and fragments of the above also are included.

The present inventions are not limited to any particular type of cell for recombinant protein production. Examples of cell types suitable for recombinant protein production include mammalian cells, insect cells, avian cells, bacterial cells, and yeast cells. The cells may be stem cells or recombinant cells transformed with a vector for recombinant gene expression, or cells transfected with a virus for producing viral products. The cells may contain a recombinant heterologous polynucleotide construct that encodes a protein of interest. That construct can be an episome or it can be an element that is physically integrated into the genome of the cell. The cells may also produce a protein of interest without having that protein encoded on a heterologous polypeptide construct. In other words, the cell may naturally encode the protein of interest, such as a B-cell producing an antibody. The cells may also be primary cells, such as chicken embryo cells, or primary cell lines.

Examples of useful cells include CHO, COS, retinal cell, Vero, CV1, kidney, HeLa, HepG2, WI38, MRC 5, Colo25, HB 8065, HL-60, lymphocyte, A431, CV-1, U937, 3T3, L cell, C127 cell, SP2/0, NS-0, MMT cell, stem cell, tumor cell, and a cell line derived from an aforementioned cell. In various embodiments, the cell line is a CHO cell derivative, such as CHO-K1, CHO DUX B-11, CHO DG-44, Veggie-CHO, GS-CHO, S-CHO, or CHO lec mutant lines.

A production phase can be conducted at any scale of culture, from shaker flasks or wave bags, to one-liter bioreactors, and to large scale industrial bioreactors. Likewise, a seed train expansion phase can be conducted at any scale of culture, from and shaker flasks or wave bags, to one-liter or larger bioreactors. A large scale process can be conducted in a volume of about 100 liters to 20,000 liters or more. One or more of several means may be used to control protein production, such as temperature shift or chemical induction. A growth phase may occur at a higher temperature than a production phase. For example, a growth phase may occur at a first temperature of about 35° C. to 38° C., and a production phase may occur at a second temperature of about 29° C. to 37° C., optionally from about 30° C. to 36° C. or from about 30° C. to 34° C. In addition, chemical inducers of protein production, such as caffeine, butyrate, tamoxifen, estrogen, tetracycline, doxycycline, and hexamethylene bisacetamide (HMBA), may be added concurrent with, before, or after a temperature shift. If inducers are added after a temperature shift, they can be added from one hour to five days after the temperature shift, such as from one to two days after the temperature shift. Production cell cultures may be run as continuous feed culture system, as in a chemostat (see C. Altamirano et al., 2001 supra), or according to a fed-batch process (Huang, 2010 supra).

Media and Buffer Selection

Yet other aspects of the inventions relate to methods for screening cell culture media or HEPES buffer for selection for use in cell culture to thereby improve cell culture performance, e.g., improved protein titer, improved cell growth, improved viable cell density, etc. Such methods may be used to select media having reduced impurities according to the inventions for use in cell culture, or to select HEPES buffer having reduced impurities for use in cell culture.

In some embodiments, a method is provided for selecting a cell culture medium for use in cell culture to improve cell culture performance. The method may generally include: providing a cell culture medium comprising HEPES buffer; analyzing the cell culture medium comprising the HEPES buffer to determine the amount of a HEPES related impurity having a molecular weight (MW) of 267.07 and the amount of a HEPES related impurity having a molecular weight (MW) of 221.06 present in the cell culture medium; and selecting the cell culture medium comprising the HEPES buffer for use in cell culture if the cell culture medium comprising the HEPES buffer is determined to have the reduced HEPES related impurities discussed herein. In accordance with the inventions, the use of a cell culture medium selected in accordance with such method improves cell culture performance, relative to cell culture performance in a non-HEPES impurity reduced cell culture media.

In other embodiments, a method is provided for selecting HEPES buffer for use in cell culture to improve cell culture performance. The method may generally include: providing a HEPES buffer; analyzing the HEPES buffer to determine the amount of a HEPES related impurity having a molecular weight (MW) of 267.07 and the amount of a HEPES related impurity having a molecular weight (MW) of 221.06 present in the HEPES buffer; and selecting the HEPES buffer for use in cell culture if the HEPES buffer is determined to have the reduced HEPES related impurities discussed herein. In accordance with the inventions, the use of a HEPES buffer selected in accordance with such method improves cell culture performance, relative to cell culture performance with non-impurity reduced HEPES buffer.

Any suitable method for analyzing the media or HEPES buffer to quantitatively determine the presence of the HEPES related impurities may be used in connection with the methods disclosed herein. Analytical methodologies for use according to the inventions include HPLC, LC-MS and other methodologies, including all analytic, separation and purification methodologies disclosed herein.

The present inventions are not limited in scope by the specific embodiments described herein, which are intended as illustrations of individual aspects or embodiments of the inventions. Functionally equivalent methods and components are within the scope of the inventions. Various modifications of the inventions, in addition to those described here, are apparent to those skilled in the art from the foregoing description and accompanying drawings. Such modifications fall within the scope of the inventions.

EXAMPLES

The following examples are provided for illustrative purposes only and are not intended to limit the scope of the inventions.

Example 1—Identification of Hepes Related Impurities

ANOVA analysis of the lot genealogy of 53 different components of a chemically defined media was performed between lots utilized in "high titer" performing cell culture runs and "low titer" performing cell culture runs. HEPES acid and salt were identified as "high risk" components, showing the strongest correlation with final titer (the correlation was stronger than the correlation between the titer and media as whole). HEPES also was identified as a "high risk component" in an independent risk-based analysis that considered the weight fractions of components in the media formulation, components' COA purity and their manufacturing methods.

As follow up, FTIR and Raman spectroscopic analyses of media lots were performed. A strong correlation was found between the absorption in certain regions of the FTIR spectra of media and final titer, which were assigned to HEPES (based on known features of HEPES spectra) and later confirmed by comparison to the FTIR spectra from HEPES retains. The spectral differences between "low titer" and "high titer" performing lots aligned with the observed titer outcomes. Data was acquired from additional media lots and used to build a predictive model for the titer performance of incoming media lots.

Several bands in Raman spectra of CDM1B were also found to have a strong correlation with final titer. Similar to FTIR analyses, these bands were assigned to HEPES by matching the Raman spectra of the media with the spectra of the HEPES retain samples.

Following identification of HEPES as a "high risk" component with strong correlation to final titer, an analysis of the chemical composition of HEPES buffer lots was performed, including LC-MS and titer correlations evaluations. Based on these studies, two HEPES related impurities were identified that showed a negative correlation to titer for all production runs analyzed.

The two identified HEPES related impurities were determined to have the chemical formula and molecular weight (MW) presented in Table 2 below.

TABLE 2

| Putative ID | Formula | m/z (Negative) |
|---|---|---|
| HEPES+[O2]−[H2] | C8 H16 N2 O6 S | 267.07 |
| HEPES−[CH4] | C7 H14 N2 O4 S | 221.06 |

Table 3 below shows the all impurities identified, including HEPES+[O2]−[H2] and HEPES−[CH4].

TABLE 3

| | | | Pearson Correlation Coefficient | | |
|---|---|---|---|---|---|
| Putative ID | Formula | m/z (Negative) | 5 HEPES salt lots | 20 CDM1B lots (Rens) | 7 CDM1B lots (Geel) |
| Vinylsulfonic acid | C2 H4 O3 S | 106.98 | −0.60 | 0.16 | 0.41 |
| HEPES+[O2]−[H2] | C8 H16 N2 O6 S | 267.07 | −0.82 | −0.77 | −0.68 |
| HEPES+[O]−[H2] | C8 H16 N2 O5 S | 251.07 | −0.80 | 0.17 | −0.22 |
| HEPES−[CH4] | C7 H14 N2 O4 S | 221.06 | −0.85 | −0.68 | −0.83 |
| Acetamidomethane-sulfonic acid | C3 H7 N O4 S | 152.00 | −0.81 | −0.78 | −0.34 |
| HEPES+[O] | C8 H18 N2 O5 S | 253.09 | −0.95 | −0.20 | −0.03 |
| 2,2-Dihydroxyethane-sulfonic acid | C2 H6 O5 S | 140.99 | −0.85 | NA | NA |
| HEPES−[C2H6]+[O] [SO3 containing] species | C6 H12 N2 O5 S | 223.04 | −0.74 | NA | NA |

Surprisingly, the impurities identified below in Table 4 (Table 4 compounds) did not have an adverse effect on cell titer even though many had a great presence than HEPES+[O2]−[H2] and HEPES−[CH4]. One of more of the Table 4 compounds can be present in the culture medium without having an unduly adverse effect on the cells.

TABLE 4

| Putative ID |
|---|
| Vinylsulfonic acid |
| HEPES+[O]−[H2] |
| Acetamidomethane-sulfonic acid |
| HEPES+[O] |
| 2,2-Dihydroxyethane-sulfonic acid |
| HEPES−[C2H6]+[O] |
| [SO3 containing] species |

While not intending to be limited by theory, based on the chemical formula and molecular weight (MW), the following chemical structures are proposed for the HEPES related impurities. However, the inventions are not limited to the presentation of these proposed chemical structures, and other chemical structures corresponding to the chemical formulas and molecular weights of the HEPES related impurities are envisioned as within the scope of the inventions.

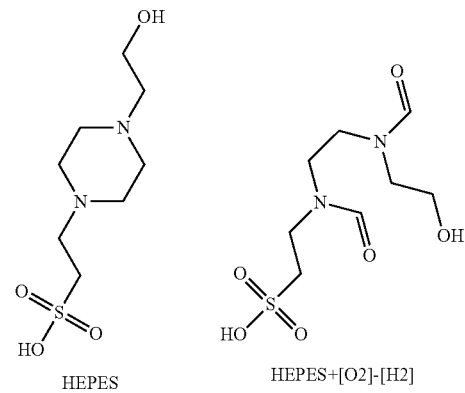

-continued

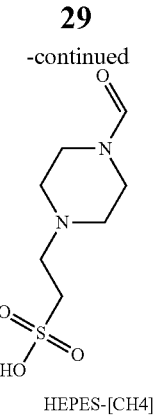

HEPES-[CH4]

Example 2—Hepes Related Impurities Negatively Correlated to Titer

Large scale production runs were performed at multiple sites to produce dupilumab. In accordance with the inventions, it was found that the amount of HEPES related impurities, as discussed herein, impact protein titer. Based on the findings, and in accordance with the inventions, improved protein titer may be obtained by using media having reduced HEPES related impurities, in accordance with the inventions.

Figures 2A, 2B:
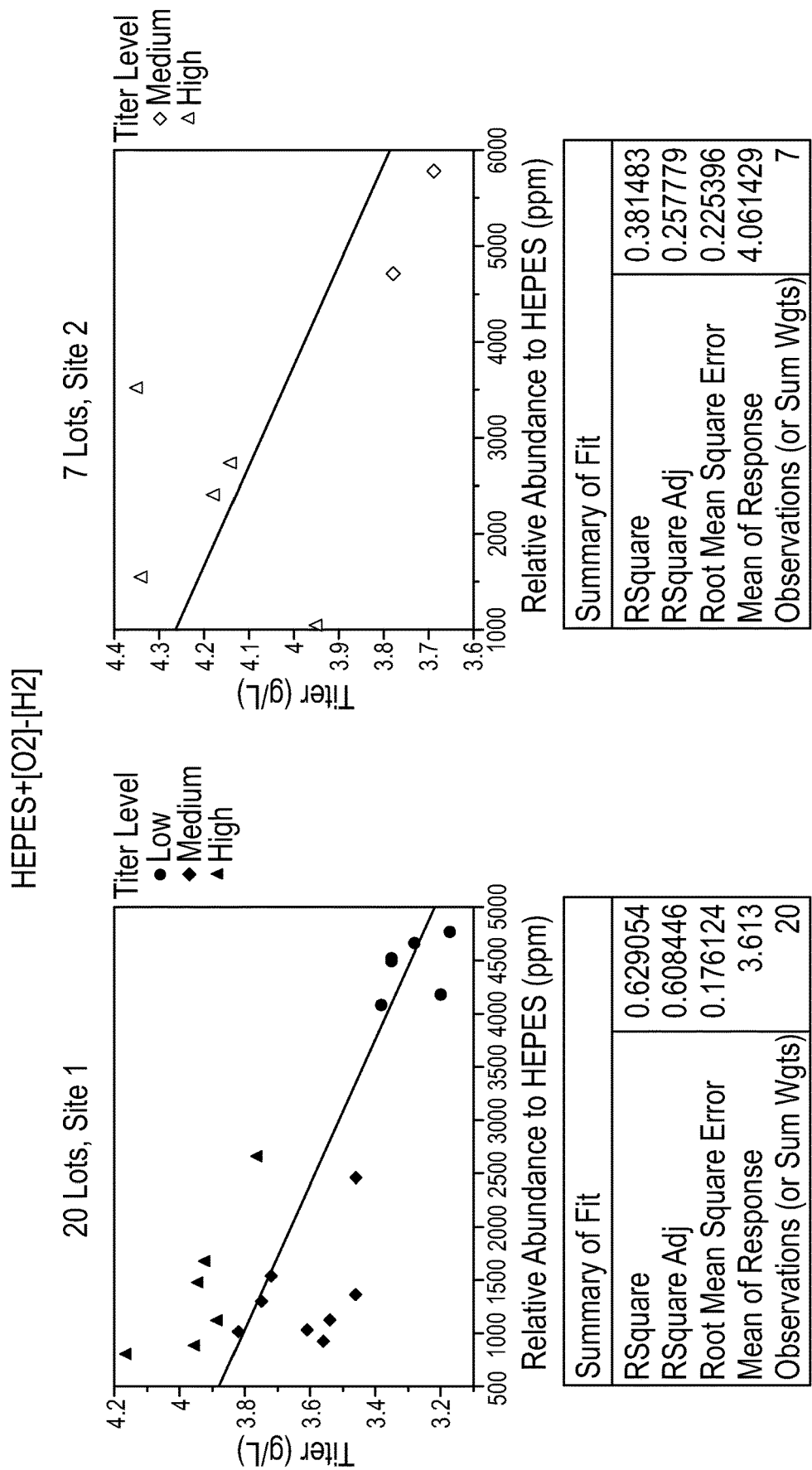
FIGS. 2A-2B illustrate a negative correlation between a HEPES related impurity and protein titer, in accordance with one embodiment of the inventions.
Figure 7:
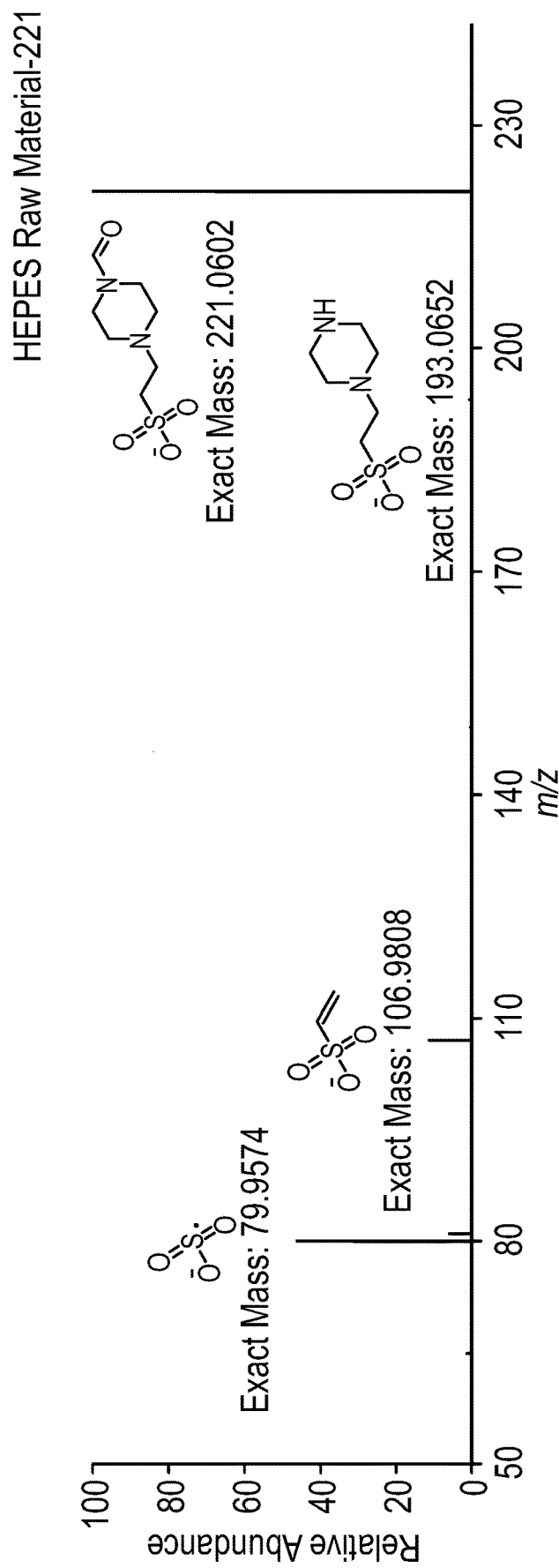
FIG. 7 show MS/MS fragmentation of HEPES–[CH4] (also referred to as "221") from HEPES raw material.

FIG. 1 illustrates the relation between relative amounts of HEPES+[O2]-[H2] and protein titer. FIGS. 2A and 2B demonstrate a negative correlation between titer and HEPES+[O2]-[H2] for multiple production runs of dupilumab at two different sites (FIG. 2A, 20 production runs at Site 1; FIG. 2B, 7 production runs at Site 2). Summary of fit data is shown below each graph of FIGS. 2A and 2B.

Figure 3:
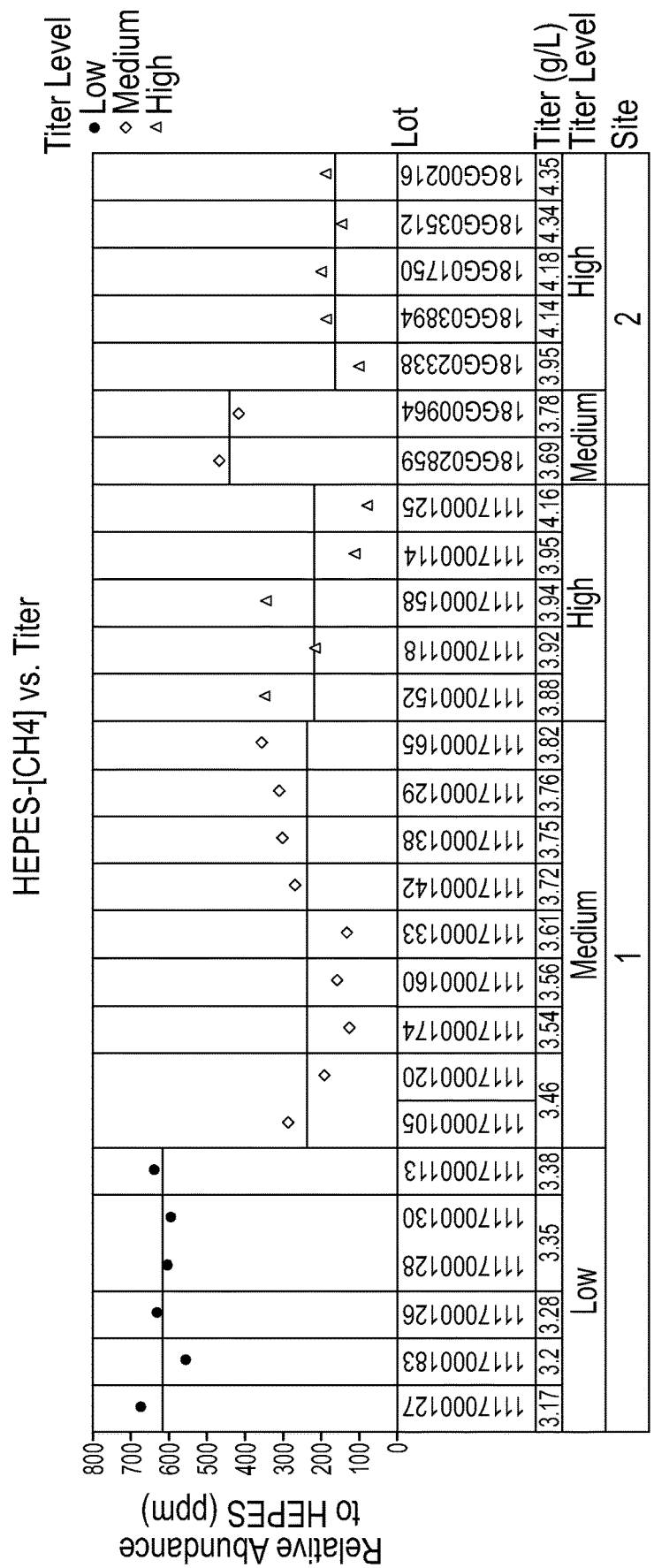
FIG. 3 illustrates the relation between a HEPES related impurity and protein titer, in accordance with one embodiment of the inventions at Sites 1 and 2.
Figures 4A, 4B:
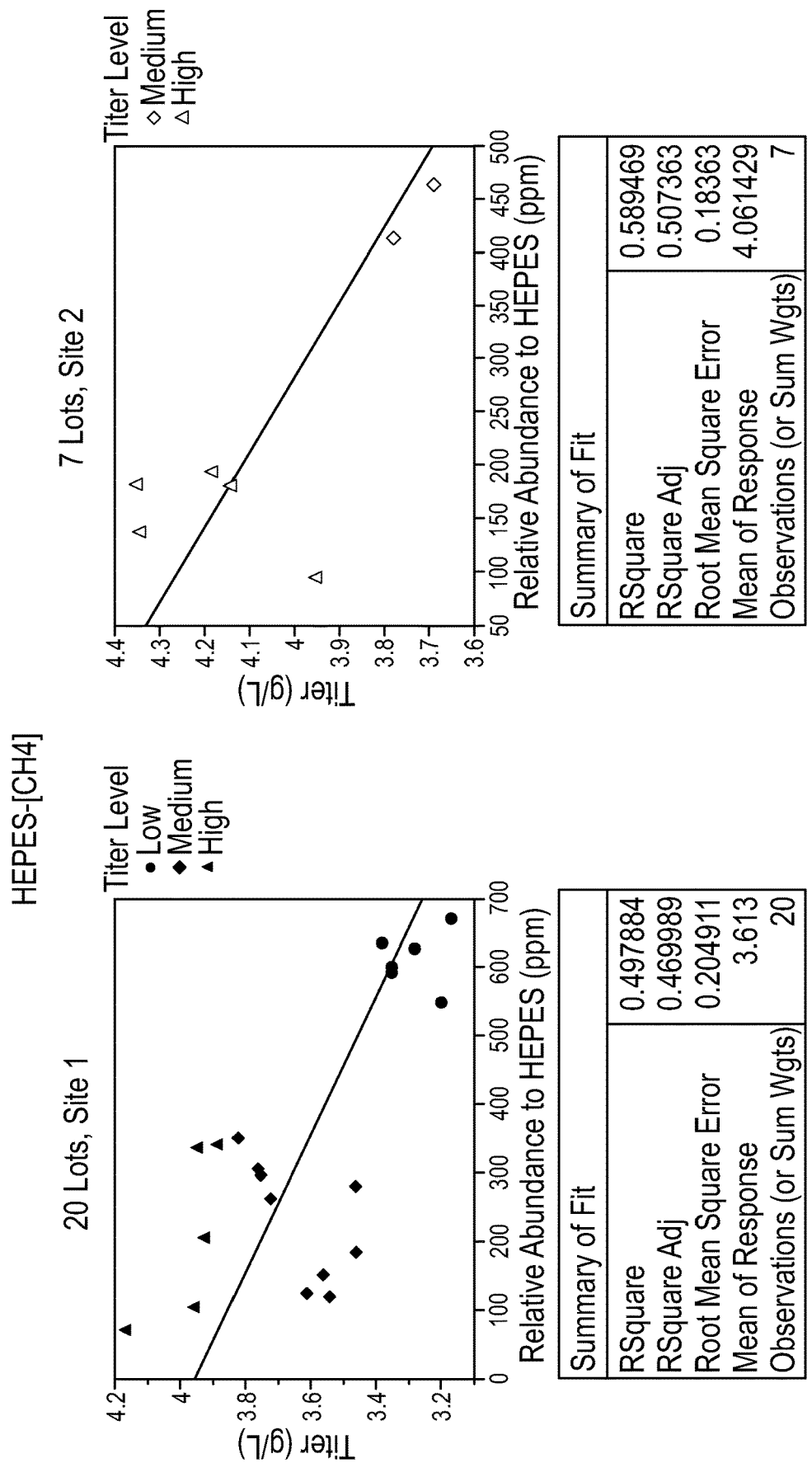
FIGS. 4A-4B illustrate a negative correlation between a HEPES related impurity and protein titer, in accordance with one embodiment of the inventions.

FIG. 3 illustrates the relation between relative amounts of HEPES-[CH4] and protein titer. FIGS. 4A and 4B demonstrate a negative correlation between titer and HEPES-[CH4] for multiple production runs of dupilumab at two different sites (FIG. 4A, 20 production runs at Site 1; FIG. 4B, 7 production runs at Site 2). Summary of fit data is shown below each graph of FIGS. 4A and 4B.

As shown in the figures, at both Site 1 and Site 2, both HEPES+[O2]-[H2] and HEPES-[CH4] showed higher abundance in lower titer production runs, and demonstrated a negative correlation with titer. The similar results seen at different production sites increases the confidence in the determination that greater abundance of HEPES+[O2]-[H2] and HEPES-[CH4] has a negative correlation with titer.

Example 3—Structure Elucidation of Impurities in Hepes Buffer

Figure 5A:
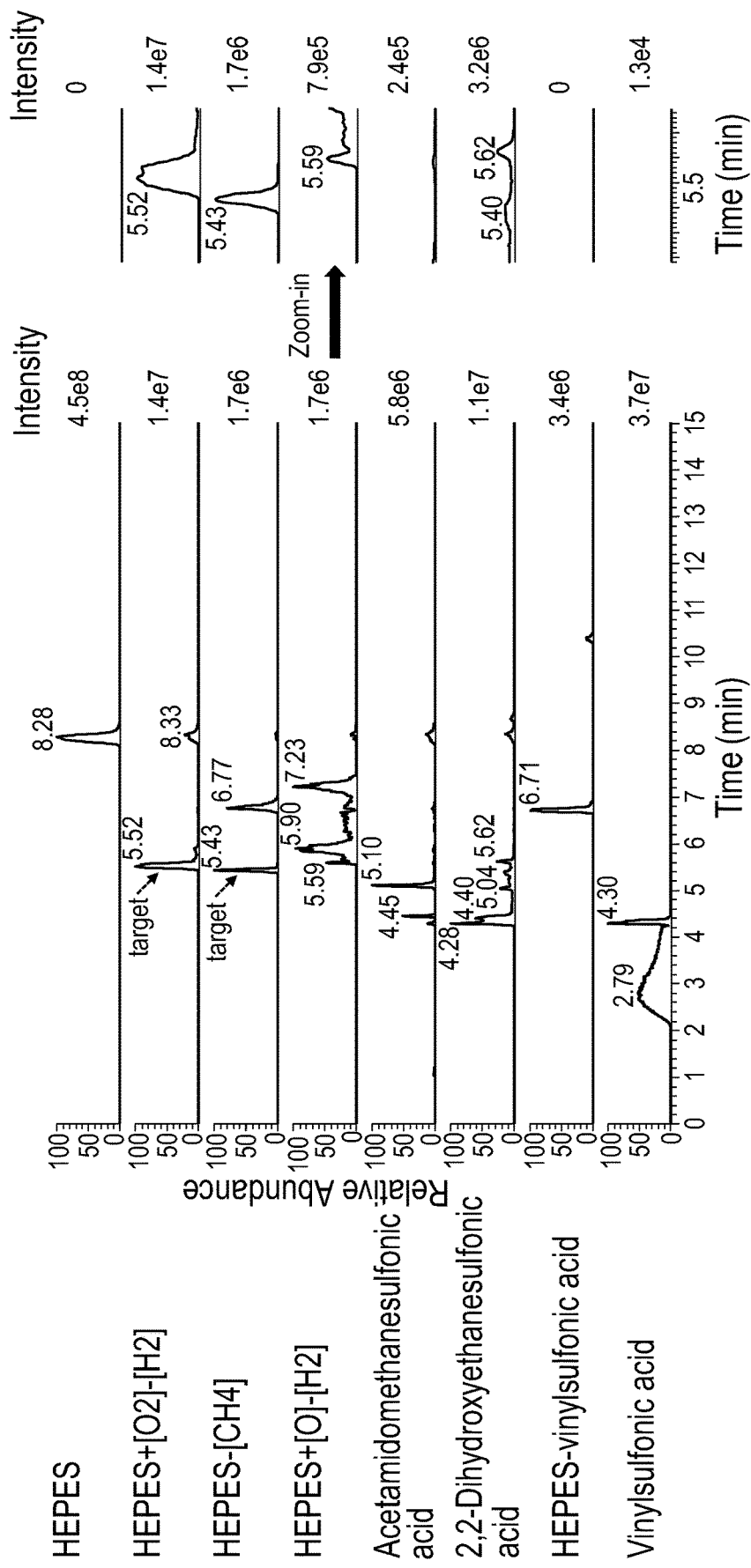
FIG. 5A illustrates the HILIC separation of HEPES impurities.
Figure 5B:
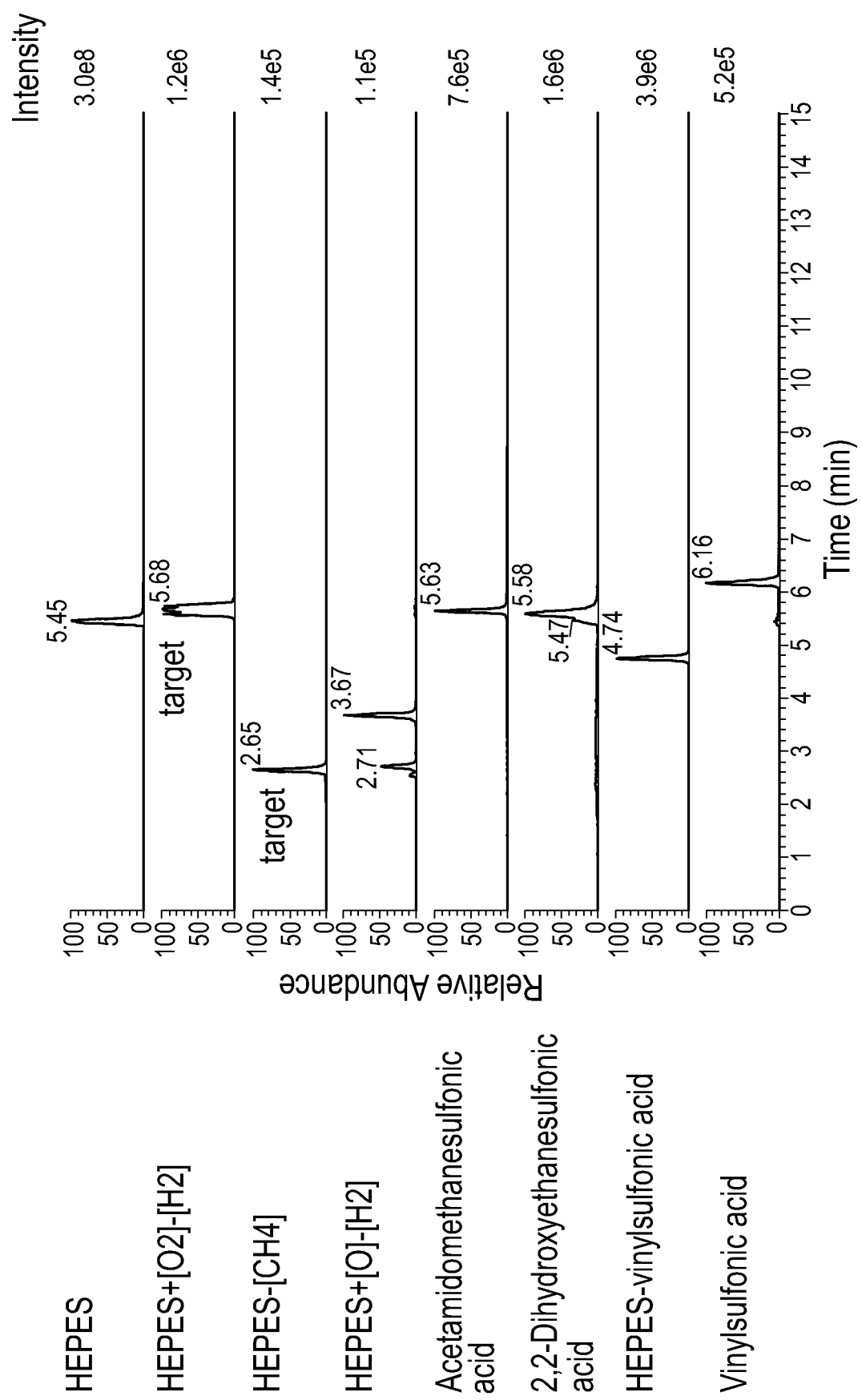
FIG. 5B illustrates the separation of HEPES impurities by mixed mode column separation.

HEPES+[O2]-[H2] and HEPES-[CH4] were separated from HEPES using a hydrophilic interaction liquid chromatography (HILIC) column (FIG. 5A showing Target). A mixed mode column was used to further separate HEPES+[O2]-[H2] and HEPES-[CH4] with other HEPES impurities which were collected in the fraction from HILIC separation (FIG. 5B showing target). The combination of both columns may be used to further purify HEPES+[O2]-[H2] and HEPES-[CH4].

Figure 6B:
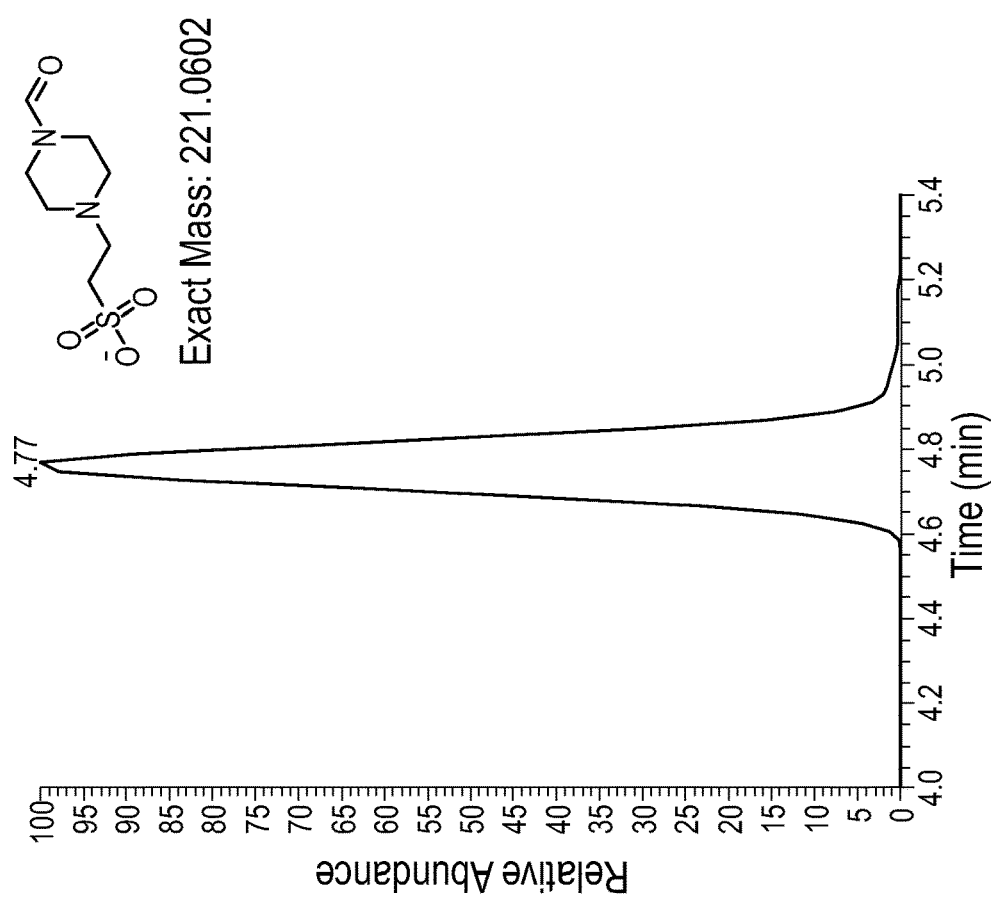
FIG. 6B is a HILIC-LCMS plot of HEPES–[CH4] from HEPES raw material.
Figure 6A:
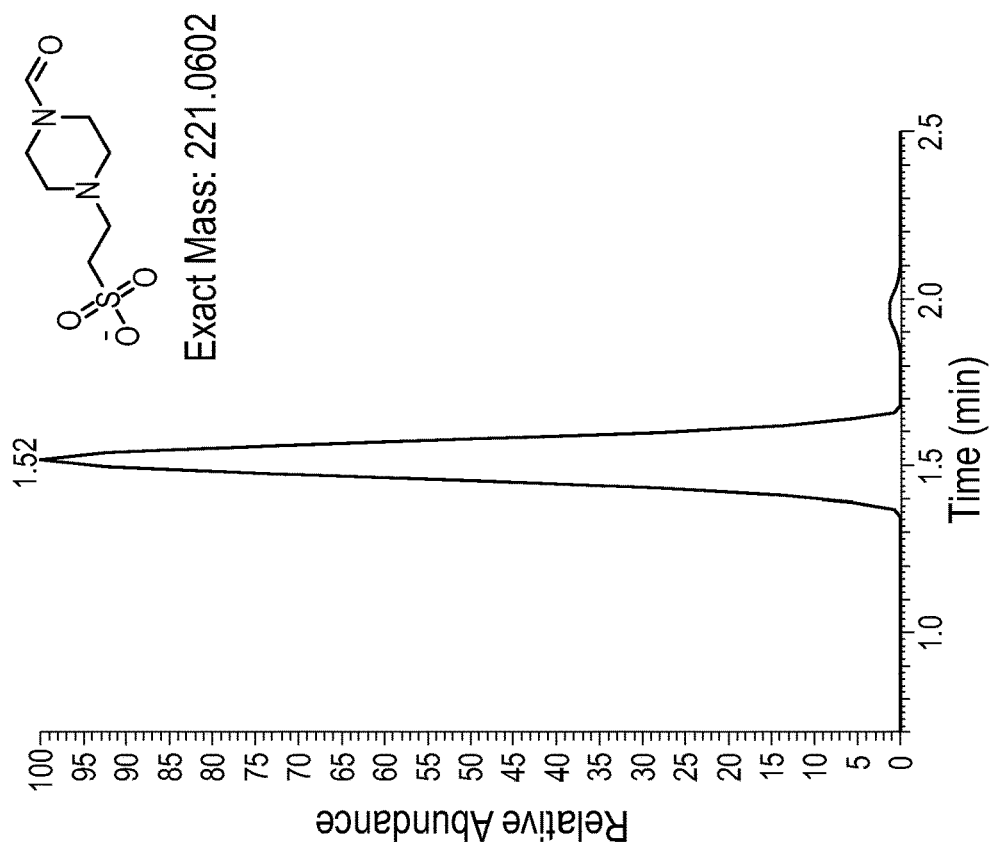
FIG. 6A is a RP-LCMS plot of HEPES–[CH4] (also referred to as "221") from HEPES raw material.

The structures of the HEPES+[O2]-[H2] and HEPES-[CH4] were confirmed using reverse phase liquid-chromatographic mass spectrometry (RP-LCMS), hydrophilic interaction liquid chromatography mas spec (HILIC-LCMS), and MS/MS fragmentation. FIG. 6A is a RP-LCMS plot of HEPES-[CH4] (also referred to as "221") sourced from HEPES raw material. FIG. 6B is a HILIC-LCMS plot of HEPES-[CH4] sourced from HEPES raw material. FIG. 7 shows MS/MS fragmentation of HEPES-[CH4] sourced from HEPES raw material.

Example 4—Proteins

The inventions can be employed in the production of biological and pharmaceutical products, and are amenable to propagation of cells comprising genes encoding proteins of interest, and each embodiment and example disclosed in this application can be used with the below-identified in the production of biological and pharmaceutical products. Such proteins can include, but are not limited to antibodies, receptors, fusion proteins, antagonists, inhibitors, enzymes (such as those used in enzyme replacement therapy), factors and co-factors, cytokines, chemokines, repressors, activators, ligands, reporter proteins, selection proteins, protein hormones, protein toxins, structural proteins, storage proteins, transport proteins, neurotransmitters and contractile proteins. Particular types of proteins that can be produced according to the inventions are discussed in greater detail below.

Antibodies (also referred to as "immunoglobulins") are examples of proteins having multiple polypeptide chains and extensive post-translational modifications. The canonical immunoglobulin protein (for example, IgG) comprises four polypeptide chains—two light chains and two heavy chains. Each light chain is linked to one heavy chain via a cysteine disulfide bond, and the two heavy chains are bound to each other via two cysteine disulfide bonds. Immunoglobulins produced in mammalian systems are also glycosylated at various residues (for example, at asparagine residues) with various polysaccharides, and can differ from species to species, which may affect antigenicity for therapeutic antibodies. Butler and Spearman, "The choice of mammalian cell host and possibilities for glycosylation engineering", Curr. Opin. Biotech. 30:107-112 (2014).

The antibody heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-10}$ M; at least $10^{-11}$ M; or at least $10^{-12}$ M, as measured by surface plasmon resonance, for example, BIACORE™ or solution-affinity ELISA.

Antibody light chains include an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain.

Light chains that can be used with these inventions include those, for example, that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

Antibody variable domains include an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

Antibody complementarity determining regions ("CDR") include an amino acid sequence encoded by a nucleic acid sequence of an organism's immunoglobulin genes that normally (i.e., in a wild-type animal) appears between two framework regions in a variable region of a light or a heavy chain of an immunoglobulin molecule (for example, an antibody or a T cell receptor). A CDR can be encoded by, for example, a germline sequence or a rearranged or not rearranged sequence, and, for example, by a naive or a mature B cell or a T cell. In some circumstances (for example, for a CDR3), CDRs can be encoded by two or more sequences (for example, germline sequences) that are not contiguous (for example, in a nucleic acid sequence that has not been rearranged) but are contiguous in a B cell nucleic acid sequence, for example, as the result of splicing or connecting the sequences (for example, V-D-J recombination to form a heavy chain CDR3). Each of the above components of antibodies can be produced according to the inventions.

Bispecific antibodies include an antibodies capable of selectively binding two or more epitopes. Bispecific antibodies generally comprise two different heavy chains, with each heavy chain specifically binding a different epitope—either on two different molecules (for example, antigens) or on the same molecule (for example, on the same antigen). If a bispecific antibody is capable of selectively binding two different epitopes (a first epitope and a second epitope), the affinity of the first heavy chain for the first epitope will generally be at least one to two, three or four orders of magnitude lower than the affinity of the first heavy chain for the second epitope, and vice versa. The epitopes recognized by the bispecific antibody can be on the same or a different target (for example, on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes, and can be produced according to the inventions.

For example, for antibody embodiments, the inventions are amendable for research and production use for diagnostics and therapeutics based upon all major antibody classes, namely IgG, IgA, IgM, IgD and IgE. IgG is a preferred class, such as IgG1 (including IgG1λ and IgG1κ), IgG2 and IgG4. Exemplary antibodies to be produced according to the inventions include Alirocumab, Atoltivimab, Maftivimab, Odesivimab, Odesivivmab-ebgn, Casirivimab, Imdevimab, Cemiplimab, Cemplimab-rwlc, Dupilumab, Evinacumab, Evinacumab-dgnb, Fasimumab, Nesvacumab, Trevogrumab, Rinucumab and Sarilumab. Further antibody embodiments include a human antibody, a humanized antibody, a chimeric antibody, a monoclonal antibody, a multi-specific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In additional embodiments, the antibody is selected from the group consisting of an anti-Programmed Cell Death 1 antibody (for example an anti-PD1 antibody as described in U.S. Pat. Appln. Pub. No. US2015/0203579A1), an anti-Programmed Cell Death Ligand-1 (for example an anti-PD-L1 antibody as described in in U.S. Pat. Appln. Pub. No. US2015/0203580A1), an anti-Dll4 antibody, an anti-Angiopoetin-2 antibody (for example an anti-ANG2 antibody as described in U.S. Pat. No. 9,402,898), an anti- Angiopoetin-Like 3 antibody (for example an anti-AngPtl3 antibody as described in U.S. Pat. No. 9,018,356), an anti-platelet derived growth factor receptor antibody (for example an anti-PDGFR antibody as described in U.S. Pat. No. 9,265,827), an anti-Erb3 antibody, an anti-Prolactin Receptor antibody (for example anti-PRLR antibody as described in U.S. Pat. No. 9,302,015), an anti-Complement 5 antibody (for example an 25 anti-C5 antibody as described in U.S. Pat. Appln. Pub. No US2015/0313194A1), an anti-TNF antibody, an anti-epidermal growth factor receptor antibody (for example an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (for example an anti-PCSK9 antibody as described in U.S. Pat. No. 8,062,640 or U.S. Pat. Appln. Pub. No. US2014/0044730A1), an anti-Growth And Differentiation Factor-8 antibody (for example an anti-GDF8 antibody, also known as anti-myostatin antibody, as described in U.S. Pat. Nos. 8,871,209 or U.S. Pat. No. 9,260,515), an anti-Glucagon Receptor (for example anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S.

Pat. Nos. 8,735,095 or U.S. Pat. No. 8,945,559), an anti-interleukin 6 receptor antibody (for example an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (for example anti- IL33 antibody as described in U.S. Pat. Appln. Pub. Nos. US2014/0271658A1 or US2014/0271642A1), an anti-Respiratory syncytial virus antibody (for example anti-RSV antibody as described in U.S. Pat. Appln. Pub. No. US2014/0271653A1), an anti-Cluster of differentiation 3 (for example an anti-CD3 antibody, as described in U.S. Pat. Appln. Pub. Nos. US2014/0088295A1 and US20150266966A1, and in U.S. application Ser. No. 62/222,605), an anti-Cluster of differentiation 20 (for example an anti-CD20 antibody as described in U.S. Pat. Appln. Pub. Nos. US2014/0088295A1 and US20150266966A1, and in U.S. Pat. No. 7,879,984), an anti-CD19 antibody, an anti-CD28 antibody, an anti-Cluster of Differentiation 48 (for example anti-CD48 antibody as described in U.S. Pat. No. 9,228,014), an anti-Fel d1 antibody (for example as described in U.S. Pat. No. 9,079,948), a SARS-CoV-2 treatment (REGN-COV™ comprising casirivimab and imdevimab), an anti-Middle East Respiratory Syndrome virus (for example an anti-MERS antibody as described in U.S. Pat. Appln. Pub. No. US2015/0337029A1), An antibody cocktail against Ebola ((REGN-EB3 comprising atoltivimab, maftivimab and odesivimab-ebgn (INMAZEB®)), an anti-Ebola virus antibody (for example, as described in U.S. Pat. Appln. Pub. No. US2016/0215040), an anti-Zika virus antibody, an anti-Lymphocyte Activation Gene 3 antibody (for example an anti-LAG3 antibody, or an anti-CD223 antibody), an anti-Nerve Growth Factor antibody (for example an anti-NGF antibody as described in U.S. Pat. Appln. Pub. No. US2016/0017029 and U.S. Pat. Nos. 8,309,088 and 9,353,176) and an anti-Activin A antibody. In some embodiments, the bispecific antibody is selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (for example, an anti-CD3×anti-Muc16 bispecific antibody), and an anti-CD3×anti-Prostate-specific membrane antigen bispecific antibody (for example, an anti-CD3×anti-PSMA bispecific antibody). See also U.S. Patent Publication No. US 2019/0285580 A1.

Antibody derivatives and fragments are amendable for production according to the inventions, and include, but are not limited to: antibody fragments (for example, ScFv-Fc, dAB-Fc, half antibodies), multispecifics (for example, IgG-ScFv, IgG-dab, ScFV-Fc-ScFV, tri-specific) and Fc-Fusion Proteins (for example, Fc-Fusion (N-terminal), Fc-fusion (C-terminal), mono Fc-fusion, bi-specific Fc-fusion).The phrase "Fc-containing protein" includes antibodies, bispecific antibodies, antibody derivatives containing an Fc, antibody fragments containing an Fc, Fc-fusion proteins, immunoadhesins, and other binding proteins that comprise at least a functional portion of an immunoglobulin CH2 and CH3 region. A "functional portion" refers to a CH2 and CH3 region that can bind a Fc receptor (for example, an FcγR; or an FcRn, (neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Antigen binding molecules (ABMs) and ABM conjugates having non-native formats, such as Fab domains in non-native configurations can be expressed according to the inventions, and are disclosed in WO 2021/026409 A1. Multispecific binding molecules (MBMs) and MBM conjugates can be produced according to the inventions, and are disclosed in WO 2021/091953A1 and WO 2021/030680 A1.

Fc-containing proteins can comprise modifications in immunoglobulin domains, including where the modifications affect one or more effector function of the binding protein (for example, modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (for example, E or Q); 250 and 428 (for example, L or F); 252 (for example, L/Y/F/W or T), 254 (for example, S or T), and 256 (for example, S/R/Q/E/D or T); or a modification at 428 and/or 433 (for example, L/R/SI/P/Q or K) and/or 434 (for example, H/F or Y); or a modification at 250 and/or 428; or a modification at 307 or 308 (for example, 308F, V308F), and 434. In another example, the modification can comprise a 428L (for example, M428L) and 434S (for example, N434S) modification; a 428L, 259I (for example, V259I), and a 308F (for example, V308F) modification; a 433K (for example, H433K) and a 434 (for example, 434Y) modification; a 252, 254, and 256 (for example, 252Y, 254T, and 256E) modification; a 250Q and 428L modification (for example, T250Q and M428L); a 307 and/or 308 modification (for example, 308F or 308P).

As stated above, the inventions also are amenable to the production of other molecules, including fusion proteins. These proteins can comprise part or all of two or more proteins, one of which is an Fc portion of an immunoglobulin molecule, that are not fused in their natural state. Fc-fusion proteins include Fc-Fusion (N-terminal), Fc-Fusion (C-terminal), Mono Fc-Fusion and Bi-specific Fc-Fusion. Preparation of fusion proteins comprising certain heterologous polypeptides fused to various portions of antibody-derived polypeptides (including the Fc domain) has been described, for example, by Ashkenazi et al., Proc. Natl. Acad. Sci USA 88: 10535-39 (1991); Byrn et al., Nature 344:677-70, 1990; and Hollenbaugh et al., "Construction of Immunoglobulin Fusion Proteins", in Current Protocols in Immunology, Suppl. 4, pages 10.19.1-10.19.11 (1992). Receptor Fc-containing proteins also are described in C. Huang, "Receptor-Fc fusion therapeutics, traps, and MFMETIBODY technology," 20(6) *Curr. Opin. Biotechnol.* 692-9 (2009).

Receptor Fc-fusion proteins comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). Some receptor Fc-fusion proteins may contain ligand binding domains of multiple different receptors.

In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (for example, rilonacept, which contains the IL-1RAcP ligand binding region fused to the Il-1R1 extracellular region fused to Fc of hIgG1; see U.S. Pat. No. 6,927,044, or a VEGF trap (for example, aflibercept or ziv-aflibercept, which contains the Ig domain 2 of the VEGF receptor Flt1 fused to the Ig domain 3 of the VEGF receptor Flk 1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen binding domain(s), such as a variable heavy chain fragment and a variable light chain fragment, of an antibody coupled to an Fc moiety.

Mini-trap protein are trap proteins that use a multimerizing component (MC) instead of a Fc portion, and are disclosed in U.S. Pat. Nos. 7,279,159 and 7,087,411, and can be produced according to the inventions.

While the inventions have been described with reference to exemplary embodiments, it will be understood by those skilled in the art that various changes may be made and equivalents may be substituted for elements thereof without departing from the scope of the inventions. In addition, many modifications may be made to adapt a particular situation or material to the teachings without departing from the essential scope thereof. Therefore, it is intended that the inventions not be limited to the particular embodiment disclosed as the best mode contemplated for carrying out these inventions, but that the inventions will include all embodiments falling within the scope of the appended claims.

What is claimed:

1. A method for selecting a cell culture medium with reduced impurities for use in cell culture to improve cell culture performance, wherein the cell culture comprises at least one recombinant eukaryotic cell that can express a recombinant protein, the method comprising:
   (a) providing a cell culture medium comprising a 4-hydroxyethyl piperazine ethanesulfonic acid (HEPES) buffer;
   (b) analyzing the cell culture medium comprising the HEPES buffer to determine the amount of HEPES related impurities HEPES+[O2]−[H2] and HEPES-[CH4] present in the cell culture medium;
   (c) selecting the cell culture medium comprising the HEPES buffer for use in cell culture if the cell culture medium comprising the HEPES buffer is determined to have less than 4000 µmol of HEPES+[O2]−[H2] per mole of total HEPES, and less than 400 µmol of HEPES-[CH4] per mole of total HEPES;
   wherein the use of the cell culture medium comprising the HEPES buffer having less than 4000 µmol of HEPES+[O2]−[H2] per mole of total HEPES, and less than 400 µmol of HEPES-[CH4] per mole of total HEPES improves cell culture performance, as compared to cell culture performance in non-HEPES related impurity reduced media.

2. The method of claim 1, wherein the improved cell culture performance comprises at least one selected from the group consisting of improved protein titer and cell growth.

3. The method of claim 1, wherein the eukaryotic cell is selected from the group consisting of mammalian cell, avian cell, insect cell, and yeast cell.

4. The method of claim 1, wherein the eukaryotic cell is selected from the group consisting of CHO, COS, retinal cell, Vero, CV1, kidney, HeLa, HepG2, WI38, MRC 5, Colo25, HB 8065, HL-60, lymphocyte, A431, CV-1, U937, 3T3, L cell, C127 cell, SP2/0, NS-0, MMT cell, stem cell, tumor cell, and a cell line derived from an aforementioned cell.

5. The method of claim 1, wherein the eukaryotic cell is a CHO cell.

6. The method of claim 1, wherein the recombinant protein is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab)'2 fragment, an IgD antibody, an IgE antibody, an IgM antibody, an IgG antibody, an IgG1 antibody, an IgG2 antibody, an IgG3 antibody, or an IgG4 antibody.

7. The method of claim 1, wherein the recombinant protein comprises an Fc domain.

8. The method of claim 1, wherein the recombinant protein is selected from the group consisting of an Fc-fusion protein, a receptor-Fc-fusion protein (TRAP), an antibody, an antibody fragment, and a ScFv-Fc fusion protein.

9. The method of claim 8, wherein the recombinant protein is selected from the group consisting of an anti-PD1 antibody, an anti-PDL-1 antibody, an anti-Dll4 antibody, an anti-ANG2 antibody, an anti-AngPtl3 antibody, an anti-PDGFR antibody, an anti-Erb3 antibody, an anti-PRLR antibody, an anti-TNF antibody, an anti-EGFR antibody, an anti-PCSK9 antibody, an anti-GDF8 antibody, an anti-GCGR antibody, an anti-VEGF antibody, an anti-IL1R antibody, an anti-IL4R antibody, an anti-IL6R antibody, an anti-IL1 antibody, an anti-IL2 antibody, an anti-IL3 antibody, an anti-IL4 antibody, an anti-IL5 antibody, an anti-IL6 antibody, an anti-IL7 antibody, an anti-RSV antibody, an anti-NGF antibody, an anti-CD3 antibody, an anti-CD20 antibody, an anti-CD19 antibody, an anti-CD28 antibody, an anti-CD48 antibody, an anti-CD3/anti-CD20 bispecific antibody, an anti-CD3/anti-MUC16 bispecific antibody, and an anti-CD3/anti-PSMA bispecific antibody.

10. The method of claim 8, wherein the recombinant protein is selected from the group consisting of alirocumab, atoltivimab, maftivimab, odesivimab, odesivivmab-ebgn, casirivimab, imdevimab, cemiplimab, cemplimab-rwlc, dupilumab, evinacumab, evinacumab-dgnb, fasimumab, nesvacumab, trevogrumab, rinucumab and sarilumab.

11. The method of claim 10, wherein the recombinant protein is dupilumab.

12. The method of claim 8, wherein the recombinant protein is aflibercept.

13. The method of claim 1, wherein the analyzing is performed by at least one selected from the group consisting of HPLC and LC-MS.

* * * * *